US006962982B2

(12) United States Patent
Scholz et al.

(10) Patent No.: US 6,962,982 B2
(45) Date of Patent: Nov. 8, 2005

(54) SOLUBLE COMPLEXES OF TARGET PROTEINS AND PEPTIDYL PROLYL ISOMERASE CHAPERONES AND METHODS OF MAKING AND USING THEM

(75) Inventors: Christian Scholz, Penzberg (DE); Herbert Andres, Penzberg (DE); Elke Faatz, Huglfing (DE); Alfred Engel, Tutzing (DE); Dorothea Sizmann, Penzberg (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 502 days.

(21) Appl. No.: 10/179,905

(22) Filed: Jun. 24, 2002

(65) Prior Publication Data

US 2003/0176665 A1 Sep. 18, 2003

Related U.S. Application Data

(63) Continuation-in-part of application No. 10/167,774, filed on Jun. 10, 2002, now abandoned.

(30) Foreign Application Priority Data

Jun. 22, 2001 (EP) ............................................. 01115225
Aug. 31, 2001 (EP) ............................................. 01120939

(51) Int. Cl.⁷ ......................... A61K 38/24; C07K 14/00

(52) U.S. Cl. ..................................... 530/399; 530/350

(58) Field of Search .................................. 530/399, 350

(56) References Cited

U.S. PATENT DOCUMENTS

| | | | |
|---|---|---|---|
| 4,735,896 A | 4/1988 | Wang et al. .................... | 435/5 |
| 4,879,212 A | 11/1989 | Wang et al. .................... | 435/5 |
| 4,945,042 A | 7/1990 | Gelger et al. | |
| 5,908,626 A | 6/1999 | Chang et al. | |
| 6,207,420 B1 | 3/2001 | Harrison et al. | |
| 6,316,405 B1 | 11/2001 | Rich et al. | |

FOREIGN PATENT DOCUMENTS

| | | |
|---|---|---|
| EP | 0 293 249 B1 | 8/1992 |
| EP | 0 280 211 B1 | 11/1994 |
| EP | 0 396 559 B1 | 8/1996 |
| EP | 1 077 262 | 2/2001 |
| WO | WO 92/22573 | 12/1992 |
| WO | WO 93/21346 | 10/1993 |
| WO | WO 93/25533 | 12/1993 |
| WO | WO 94/08012 | 4/1994 |
| WO | WO 97/10253 | 3/1997 |
| WO | WO 98/01349 | 1/1998 |
| WO | WO 98/13496 | 4/1998 |
| WO | WO 00/20606 | 4/2000 |
| WO | WO 00/26251 | 5/2000 |
| WO | WO 00/280110 | 5/2000 |

OTHER PUBLICATIONS

Otteken, et al. *Calreticulin Interacts With Newly Synthesized Human Immunodeficiency Virus Type 1 Envelope Glycoprotein, Suggesting A Chaperone Function Similar To That Of Calnexin,* The Journal of Biological Chemistry, vol. 271, No. 1, Jan. 5, 1996, pp. 97–103.

Bardwell, J., *Building Bridges: Disulphide Bond Formation in the Cell,* Molecular Microbiology (1994) 14(2), 199–205.

Beissinger, M., et al., *How Chaperones Fold Proteins, Biol. Chem., vol. 379, pp. 245–259, Mar. 1998.*

Bothmann, H., et al., *The Periplasmic Escherichia coli Peptidylprolyl cis,trans–Isomerase FkpA,* The Journal of Biological Chemistry, vol. 275, No. 22, Issue of Jun. 2, pp. 17100–17105, 2000.

Braden, B., et al., *Structural Features of the Reactions Between Antibodies and Protein Antigens,* The FASEB Journal, pp. 9–16, vol. 9, Jan. 1995.

Buchner, J., *Supervising The Fold: Functional Principles of Molecular Chaperones,* The FASEB Journal, pp. 10–19, vol. 10, Jan. 1996.

Butler, J.E., et al., *The Physical and Functional Behavior of Capture Antibodies Adsorbed on Polystyrene,* Journal of Immunological Methods, 150 (1992), 77–90.

Caffrey, M., et al., *Biophysical Characterization of gp41 Aggregates Suggests a Model for the Molecular Mechanism of HIV–Associated Neurological Damage and Dementia,* The Journal of Biological Chemist, vol. 275, No. 26, Issue of Jun. 30, pp. 19877–19882, 2000.

Chan, D., et al., *Core Structure of gp41 From The HIV Envelope Glycoprotein,* Cell, vol., 89, 263–273, Apr. 18, 1997.

Crooke, E., et al., *Trigger Factor: A Soluble Protein That Folds Pro–OmpA Into A Membrane–Assembly–Competent Form,* Biochemistry, vol., 84, pp. 5216–5220, Aug. 1987.

Danese, P., et al., *The Cpx Two–Component Signal Transduction Pathway of Escherichia Coli Regulates Transcription of the Gene Specifying the Stress–Inducible Periplasmic Protease, DegP,* Genes & Development, pp. 387–398 (1995).

(Continued)

*Primary Examiner*—Karen Cochrane Carlson
(74) *Attorney, Agent, or Firm*—Brinks Hofer Gilson & Lione

(57) ABSTRACT

The present invention relates to the diagnosis of HIV infections. It especially teaches the production of a soluble retroviral surface glycoprotein- (or transmembrane glycoprotein)-chaperone complex and the advantageous use of a chaperone-antigen complex especially in the detection of antibodies to HIV in immunoassays, preferably according to the double antigen bridge concept, or as an immunogen. The invention also discloses soluble complexes comprising a variant of HIV-1 gp41 or a variant of HIV-2 gp36, respectively, and a chaperone selected from the peptidyl-prolyl-isomerase class of chaperones. Variants comprising specific amino-acid substitutions in the N-helical domain of HIV-1 gp41 or of HIV-2 gp36, respectively, are also described.

42 Claims, 8 Drawing Sheets

OTHER PUBLICATIONS

Figure 1A:
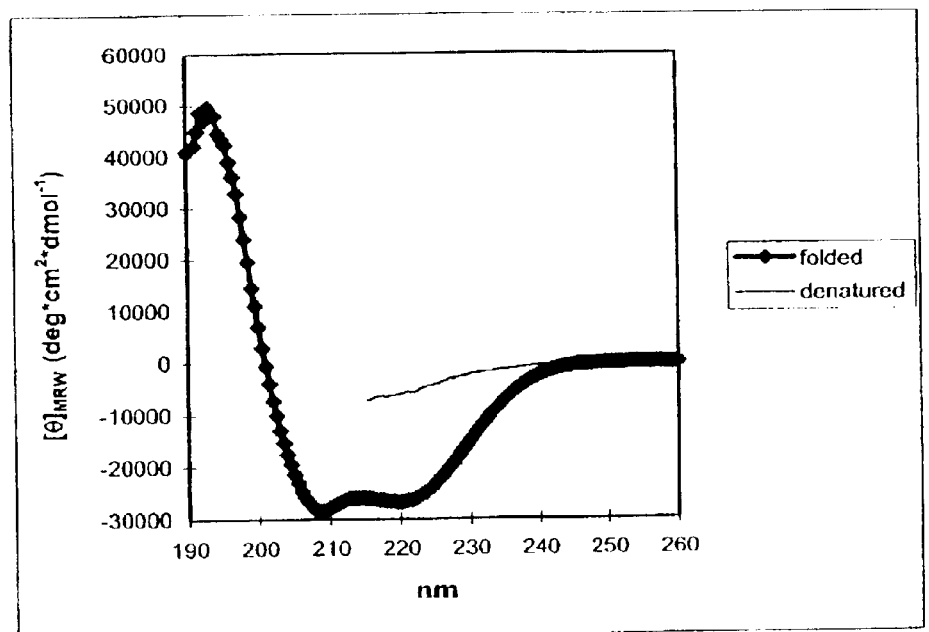

Dartigalongue, C., et al., *A New Heat–Shock Gene, ppiD, Encodes a Peptidyl–Prolyl Isomerase Required For Foling of Outer Membrane Proteins in Escherichia Coli,* The EMBO Journal, vol. 17, No. 14, pp. 3968–2980, 1998.

Dent, A., et al., *The Preparation of Protein—Protein Conjugates,* Heterobifunctional Reagents Based on the Biotin–Avidin Interaction, Chapter 5, pp. 261–363.

Doms, R., et al., *HIV–1 Membrane Fusion: Targets of Opportunity,* The Journal of Cell Biology, pp. F9–F13, vol. 151, No. 2, Oct. 16, 2000.

Egan, D.A., et al., *Equilibrium Denaturation of Recombinant Human FK Binding Protein in Urea,* Biochemistry, pp. 1920–1927, vol. 32, No. 8, 1993.

Endrich, et al., *The V3 Loop of a Human Immunodeficiency Virus Type–1 Envelope Protein is a High–Affinity Ligand for Immunophilins Present in Human Blood,* Eur. J. Biochem., 252–441–446 (1998).

Fischer, G., *Cyclophilin and Peptidyl–Prolyl Cis–Trans Isomerase are Probably Identical Proteins,* Nature, vol. 337 Feb. 2, 1989.

Frech, C., et al. *Preferential Binding of an Unfolded Protein to DsbA,* The EMBO Journal, vol. 15, No. 2, pp. 392–396, 1996.

Gething, M., *Protein Folding in Cell,* Nature, vol. 355, Jan. 2, 1992.

Goethel, S.F., et al., *Peptide–Prolyl Cis–Trans Isomerases, a Superfamily of Ubiquitous Folding Catalysts,* Cellular and Molecular Life Sciences (CMLS), pp. 423–436, vol. 55, 1999.

Guyader, M., et al., *Genome Organization and Transactivation of the Human Immunodeficiency Virus Type 2,* Nature, vol. 326 Apr. 16, 1987.

Hottenrott, S., et al., *The Escherichia coli SlyD is a Metal Ion–Regulated Peptidyl–Prolyl Cis/Trans–Isomerase,* The Journal of Biological Chemistry, vol. 272, No. 25, Issue of Jun. 20., pp. 15697–15701, 1997.

Kay, J.E., *Structure–Function Relationships in the FK506–Binding Proteing (FKBP) Family of Peptidylproly) Cis–Trans Isomerases,* Biochem. J., (1996), 314, 361–385.

Kojouharova, M.S., et al., *Differential Binding of IgG and of a HIV gp41 Peptide by the B Chain and A Chain Globular Head Sequences of C1q, Respectively,* Journal of Immunology, 161:4352–4331.

Lane, W.S., *Complete Amino Acid Sequence of the FK506 and Rapamycin Binding Protein, FKBP, Isolated from Calf Thymus,* Journal of Protein Chemistry, pp. 151–160, vol. 10, No. 2, 1991.

Lu, Min., et al., *A Trimeric Structural Domain of the HIV–1 Transmembrane Glycoprotein,* Nature Structural Biology, pp. 1–8, vol. 2, No. 12, Dec. 1995.

Meister, S., et al., *Basic Amino Acid Residues in the V3 Loop of Simian Immunodifficiency Virus Envelope Alter Viral Coreceptor Tropism and Infectivity but Do Not Allow Efficient Utilization of CXCR4 as Entry Cofactor,* Virology, 284, 287–296 (2001).

Missiakas, D., et al., *Identification and Characterization of a New Disulfide Isomerase–Like Protein (DsbD) in Escherichia Coli,* The EMBO Journal, vol. 14, No. 14, pp. 3415–3424, 1995.

Missiakas, D., et al., *New Components of Protein Foling in Extracytoplasmic Compartments of Escherichai Coli SurA, FKpA and Skp/OmpH,* Molecular Microbiology, (1996) 21(4), pp. 871–884.

Prusiner, S.B., *Prions,* Nobel Lecture, vol. 95, pp. 13363–1383 Nov. 1998.

Rahfeld, J., et al., *Confirmation of the Existence of a Third Family Among Peptidyl–Prolyl Cisltrans Isomerases Amino Acid Sequence and Recombinant Production of Parvulin,* FEBS Letters, 352 (1994) pp. 180–184.

Ramm, K., et al., *The Periplasmic Escherichia Coli Peptidylprolyl Cis, Trans–Isomerase FkpA,* The Journal of Biological Chemistry, vol., 275, No. 22, Issue of Jun. 2, pp. 17106–17113, 2000.

Ratner, L., et al., *Complete Nucleotide Sequence of the AIDS Virus, HTLV–III,* Nature, pp. 277–284, vol. 313 Jan. 24, 1985.

Rool, M.J., et al., *Protein Design of an HIV–1 Entry Inhibitor,* Science, pp. 884–888, vol., 291, Feb. 2, 2001.

Scholz, C., et al., *Cooperation of Enzymatic and Chaperone Functions of Trigger Factor in the Catalysis of Protein Folding,* The EMBO Journal, vol. 16, No. 1, pp. 54–58, 1997.

Scholz, C.,*Autocatalytic Folding of the Folding Catalyst FKBP12,* The Journal of Biological Chemistry, vol., 271, No. 22, Issue of May 31, pp. 12703–12707, 1996.

Speth, C., et al.,*A 60 kD Heat–Shock Protein–Like Molecule Interacts with the HIV Transmembrane Glycoprotein gp41,* Molecular Immunology, 36 (1999) 619–628.

Stoller, G., et al., A Ribosome–Associated Peptidyl–Prolyl Cis/Trans Isomerase Identified As the Trigger Factor, The EMBO Journal, vol. 14, No. 20, pp. 4939–4948, 1995.

P. Tijssen, *Preparation of Enzyme–Antibody or Other Enzyme–Macromolecule Conjugates,* Practice and Theory of Enzyme Immunoassays, Chapter 11, pp. 221–279, 1985.

Wang, C., et al., *Protein Disulfide Isomerase is Both an Enzyme and a Chaperone,* The FASEB Journal, vol. 7, pp. 1515–1517, Dec. 1993.

Wild, C., et al., *A Synthetic Peptide Inhibitor of Human Immunodeficiency Virus Replication: Correlation Between Solution Structure and Viral Inhibition,* Proc. Natl. Acad. Sci., vol. 89, pp. 10537–10541, Nov. 1992.

Wingfield, P.T., et al., *The Extracellular Domain of Immunodeficiency Virus gp41 Protein: Expression in Escherichia Coli, Purification, and Crystallization,* Protein Science, p. 1653–1660 (1997).

Winter, J., *Increases Production of Human Proinsulin in the Periplasmic Space of Escherichia Coli by Fusion to DsbA,* Journal of Biotechnology, 84 (2000) 175–185.

Zarnt, T., et al., *Modular Structure on the Trigger Factor Required for High Activity in Protein Funding,* Journal of Molecular Biology (1997), 271, 827–837.

Ehrnsperger, Monika, et al., *Stabilization of Proteins and Peptides in Diagnostic Immunlogical Assays by the Molecular Chaperone Hsp25,* Analytical Biochemistry 259 (1998), pp. 218–225.

Ivery, M.T.G., *Immunophilins: Switched on Protein Binding Domains?* Med Res Rev., Nov. 2000, pp. 452–484.

Matsubara, Etsuro, et al., *Apolipoprotein J and Alzheimer's Amyloid β Solubility,* Biochem J. 316 (1996), pp. 671–679.

Pennisi, Elizabeth, *Expanding the Eukaryote's Cast of Chaperones,* Science, vol. 274, Dec. 1996 pp. 1613–1614.

Yang, Yunning, et al., *Communication The Chaperone BiP/GRP78 Binds to Amyloid Precursor Protein and Decreases Aβ40 and Aβ42 Secretion,* The Journal of Biological Chemistry, vol. 273, No. 40, Oct. 1998, pp. 25552–25555.

*Ausubel, F.M. (Editor), et al., Current Protocols in Molecular Biology, vol. 3, 2001.

Beaucage., S.L., et al., *Deoxynucleoside Phosphoramidites—A New Class of Key Intermediates for Deoxypolynucleotide Synthesis,* Department of Chemistry, University of Colorado, pp. 1859–1862.

Ellis, R.W. (Chapter 29 of "Vaccines" [Plotkin, S.A. et al. (eds) published by W.B. Saunders company (Philadelphia) in 1988, especially p. 571.

Feng et al., *Infection and Immunity,* 64(1):363–365, 1996.

Hebert et al. eds. *The Dictionary of Immunology,* Academic Press, 1995.

Kapust, R.B., et al., *Escherichia Coli Maltose–Binding Protein is Uncommonly Effective at Promoting the Solubility of Polypeptides to Which it is Fused,* Protein Science (1999), pp. 1668–1674.

Kohda et al., *Biochemical Engineering Journal,* 10:39–45, 2002; see abstract and discussion.

Maniatis, T., et al., *Molecular Cloning, A Laboratory Manual,* Cold Spring Harbor Laboratory, 1982, Table of Contents, Seven Pages.

Matteucci, M.D., et al., *Synthesis of Deoxyoligonucleotides on a Polymer Support,* Journal of the American Chemical Society, vol. 103, No. 11, 1981.

Metzger D., et al., *The Human Oestrogen Receptor Fucntions in Yeast,* Nature, pp. 31–316, vol. 334, Jul. 7, 1988.

Spreng S. and Gentschev I., "Construction of Chromosomally Encoded Secreted Hemolysin Fusions Proteins by Use of Mini–TnhylA$_6$ Transposon," *FEMS Microbiology Letters* (1998) 165:187–192.

Schein C., "Production of Soluble Recombinant Proteins in Bacteria," *Biotechnology Nature* (Nov. 1989) 7(11): 1141–1149.

*The Dictionary of Immunology,* Herbert et al eds, Academic Press, 1995.

Nishihara K. et al., "Overexpression of Trigger Factor Prevents Aggregation of Recombinant Proteins in *Escherichia coli,*" Applied and Environmental Microbiology (Mar. 2000) 66(3):884–889.

*Weir et al., *Handbook of Experimental Immunology,* vol. 1:Immunochemistry, p. 8.14–8.15.

SOLUBLE COMPLEXES OF TARGET PROTEINS AND PEPTIDYL PROLYL ISOMERASE CHAPERONES AND METHODS OF MAKING AND USING THEM

RELATED APPLICATIONS

This application is a continuation-in-part application of Ser. No. 10/167,774, filed Jun. 10, 2002, now abandoned, which claims foreign priority to European Applications EP 01115225.3, filed Jun. 22, 2001, and EP 01120939.2, filed Aug. 31, 2001. These applications are incorporated herein by reference in their entirety.

FIELD OF THE INVENTION

The present invention relates to the diagnosis of HIV infections. It especially teaches the production of a soluble retroviral surface glycoprotein- (or transmembrane glycoprotein)-chaperone complex and the advantageous use of a chaperone-antigen complex, especially in the detection of antibodies to HIV in immunoassays, preferably according to the double antigen bridge concept, or as an immunogen. The invention also discloses soluble complexes comprising a variant of HIV-1 gp41 or a variant of HIV-2 gp36, respectively, and a chaperone selected from the peptidyl-prolyl-isomerase class of chaperones. Variants comprising specific amino-acid substitutions in the N-helical domain of HIV-1 gp41 or of HIV-2 gp36, respectively, are also described.

BACKGROUND

Human Immunodeficiency Virus (HIV) is the agent of Acquired Immunodeficiency Syndrome, which is commonly referred to by its acronym AIDS. There are two major strains of this virus, designated HIV-1 and HIV-2. The HI-virus is nowadays widely disseminated and constitutes a serious threat to health and wealth worldwide, forcing public health care systems to spend tremendous amounts of money for the diagnosis of HIV and treatment of AIDS.

One of the routes for viral spread is the transfusion of infected blood or blood products. Virtually all industrialized countries, as well as many developing countries, to date require on a mandatory basis testing of all blood donations to prevent the further spread of this virus. It is the task of all diagnostic methods in the field to diagnose the infection with HIV from blood as reliably and as soon after infection as possible.

Basically, three different modes of diagnosis are available:

(1) diagnosis of viral genomic material from blood by sensitive nucleic acid diagnostic procedures like polymerase chain reaction (PCR), (2) the detection of viral antigens from blood, and (3) the detection of antibodies against HIV from bodily fluids.

During the course of an HIV infection, several diagnostically distinct and diagnostically relevant phases are known. In an early phase of infection only proteins or peptides derived from the HI virus may be found ("viraemic phase"), whereas no anti-HIV antibodies are present yet. In the subsequent phase, which is termed seroconversion, antibodies against the HIV antigens appear, while the amount of viral antigens (viral load) decreases. The majority of the antibodies formed in the early phase of the seroconversion belongs to the immunoglobulin class M (IgM). Later on the immune response against HIV switches to the immunoglobulin class G (IgG), which then builds up the majority of the antibodies directed against HIV. During the further course of infection the level of anti-HIV antibodies may decrease whereas the viral load (the presence of viral particles or viral antigens) in bodily fluids may increase again. The screening for the presence of HIV infection is preferably done with serological assays detecting antibodies against HIV antigens, sometimes combined with the detection of HIV antigen. Since the immune response within a patient changes during the course of infection and also varies from patient to patient, it is important to have extremely sensitive and reliable immunoassays detecting anti-HIV antibodies belonging to the subclasses IgM and IgG. Many different approaches for the detection of HIV infections have been described. Early, reliable and sensitive detection of antibodies against viral proteins is crucial and of major importance.

Viral proteins, which often are termed viral antigens, may be only detectable at the onset of infection and in a very late stage of the disease. Assays for detection of viral antigens, like the assays measuring p24 (from HIV-1) or p26 (from HIV-2), both of which are viral core proteins, can therefore be used only in combination with other diagnostic means to reliably detect an HIV infection.

Three groups of viral antigens are theoretically available, which may induce antibody formation in the host and thus be used as antigens in diagnostic procedures. These are the envelope proteins (encoded by the env gene region), viral enzymes or regulatory proteins such as the reverse transcriptase or integrase (encoded by the pol gene region) and structural core proteins (encoded by the gag gene region). The viral envelope proteins both in HIV-1 and HIV-2 are glycoproteins that are synthesized as polypeptide precursor proteins (gp160 for HIV and gp140 for HIV-2). These high molecular weight precursors, after synthesis, are cleaved to result in gp120 and gp41 (HIV-1) or gp110 and gp36 (HIV-2), respectively. The larger polypeptides (gp120 or gp110, respectively) form a surface subunit that is associated to the membrane spanning smaller polypeptides (gp41 and gp36, respectively) via loose contacts. In many hosts (patients), envelope glycoproteins are preferred targets of the anti-viral immune response. Ratner, L., et al., Nature 313 (1985) 277–84 have demonstrated that especially the membrane spanning of these envelope proteins, i.e., gp41 or gp36, respectively, bear the most immunogenic potential among these viral proteins.

Immunoassay methods, such as, e.g., ELISA (enzyme-linked immunosorbent assay), employing polypeptides encoded by the HI virus, have been extensively used in diagnosis and screening. The viral polypeptides are either directly prepared from viral material, or are derived from in vitro or in vivo expression systems using recombinant DNA technology. Both ways of antigen production suffer from severe limitations. Polypeptides derived from viral preparations may be contaminated by viable virus or infectious genetic material, thus posing a hazard to personnel using the material. Recombinant-derived material may be contaminated by non-HIV host proteins, which may result in reduced specificity or reduced sensitivity of such assays.

In the detection of antibodies against pathogenic agents, such as viral pathogens, very frequently and to great advantage antibody detection systems according to the double antigen bridge format, e.g., described in U.S. Pat. No. 4,945,042, are used. The immunoassays according to this bridge concept require the use of an antigen directly or indirectly bound to a solid phase and of the same or a cross-reactive readily soluble antigen that is directly or indirectly detectable. The antibodies under investigation, if present, form a bridge between the solid phase bound antigen and the labelled detection antigen. Only if the two antigens are bridged by specific antibodies a positive signal is generated.

Several attempts to use a recombinantly produced gp41 as an antigen for the detection of anti-HIV antibodies have been described. Recombinantly produced gp41, with some limitations, may be used to detect anti-HIV antibodies. Such gp41 is either used alone or in combination with other HIV antigens to measure anti-HIV antibodies. Nowadays, assays are known which independently aim at the detection of both HIV antigen and/or anti-HIV antibodies. In WO 93/21346, a "combi-test" for the simultaneous detection of gp24 antigen and antibodies to HIV-1 gp41 and HIV-2 gp36 is described. In this assay, a solid phase is used to which the recombinantly produced gp41 is directly coated.

It is also well established that the use of extraordinarily high or low pH values is one way to keep gp41 (or gp36) in solution. Recombinantly produced gp41 is known to be soluble around and below pH 3.0 or around and above pH 11.0.

Unfortunately, however, both HIV-1 gp41 and HIV-2 gp36, respectively, are essentially insoluble under physiological buffer conditions.

Immunoassays in general are performed at physiological pH. Due to their insolubility under physiological buffer conditions, retroviral surface glycoprotein antigens in many immunoassays are used directly coated onto a solid phase material. Direct coating of antigens to solid phase materials, however, is detrimental in many cases and results in disadvantages like conformational changes, molecular unfolding, change in antigenicity, instability, and in background problems (cf. Butler, J. E., et al., J. Immunol. Methods 150 (1992) 77–90).

Although it is possible to solubilize a retroviral surface glycoprotein (rsgp) by means of strongly chaotropic reagents or appropriate detergents, the material solubilized in such a manner is of limited use as a diagnostic tool.

The insolubility of retroviral surface glycoproteins at physiological buffer conditions in addition renders these proteins a very difficult target of routine (bio-)chemical procedures. The vast majority of "labeling chemistries", i.e., the chemical procedures used for binding a label, e.g., a marker group to a polypeptide, is based on nucleophilic chemistry and thus rather restricted to a pH window from about pH 6 to about pH 8 and thus only works at more or less physiological buffer conditions. These routine procedures, e.g., as described in Aslam, M. and Dent, A., The preparation of protein-protein conjugates in "Bioconjugation" (1998) 216–363, Eds. M. Aslam and A. Dent, McMillan Reference, London, either do not work properly or are difficult to carry out at the extreme pH values (or in the presence of detergents such as SDS) required to solubilize a retroviral surface glycoprotein.

As mentioned above, immunoassays according to the bridge concept have proven advantageous in a wide variety of different assays aiming at the detection of antibodies reactive with pathogenic organisms. However, due to its insolubility, it has, e.g., not been possible to use the e-gp41 molecule (i.e. "ectodomain of glycoprotein 41") of HIV-1 or e-gp36, respectively, in such an assay setup.

In order to compensate for the disadvantages of direct coating, a variety of assays have been designed, which instead of using the e-gp41 antigen, make use of synthetically or recombinantly produced partial sequences thereof, more or less spanning the immunodominant so-called loop region. Examples of such assays are given in the patent literature discussed below.

The loop region in the extracellular part of gp41 is the non-helical apical hairpin of the molecule linking the N-terminal helical domain to the likewise helical C-terminal domain. A significant part of antisera reactive to gp41 comprises antibodies to the apical loop motif. This disulfide bridged hairpin or loop structure thus represents an immunodominant region of gp41. One bypass to overcome the problems associated with recombinantly derived gp41 therefore is the chemical production of peptides representing partial sequences of gp41. It is important to note that gp41 or gp36, respectively, as referred to in the present invention is defined as the so-called ectodomain encompassing the loop-connected N- and C-helices but lacking the N-terminal fusion peptide and the C-terminal transmembrane segment.

Peptide fragments of a variety of HIV antigens are disclosed in the relevant patent literature (Australian Patent Application No. 597884 (57733/86), and in U.S. Pat. Nos. 4,735,896 and 4,879,212). In particular, these three specifications disclose a conserved immunodominant region of the gp41 glycoprotein, the loop region of the major envelope protein of HIV-1. An analogous immunodominant region of the gp36 protein of HIV-2 has also been synthesized. Peptides corresponding to these loop regions, which constitute the apex of the ectodomain, enable an early diagnosis of HIV-1 and HIV-2 and provide for assays with sufficient but not optimal sensitivity and good specificity. Their limitations, however, become evident with respect to detection of IgM antibodies during the first days of seroconversion in certain patients.

WO 92/22573 discloses peptides having immunological properties in common with the backbone, i.e., with an immunodominant region of the transmembrane envelope protein (e.g., gp41 or gp36) of various mammalian immunodeficiency viruses. It further confirms that this immunodominant region comprises a disulfide loop which is highly conserved in immunodeficiency virus isolates derived from different mammalian species.

EP 396 559 relates to artificial peptides bearing an amino acid sequence that corresponds to a naturally occurring amino acid sequence of a HIV. The epitopes again are derived from sequences corresponding to the loop structure of gp41 or gp36, respectively. They further have been refined to contain a disulfide bridge formed by a chemical oxidation step between the two cysteine residues of the immunodominant loop.

A quite significant percentage of antibodies as contained in anti-HIV antisera of HIV-infected patients, however, does not react with the sequence motif or its variants derived from the immunodominant loop of gp41 or gp36. Whereas these peptide antigens can be used in combination with the advantageous bridge concept, antibodies reactive with epitopes outside the loop region of HIV gp41 are not detected. Not only is the very early diagnosis of an HIV infection crucial, it is also extremely important that as many subtypes of HIV-1 and HIV-2 as possible be detected. The more epitopes, especially of the correctly folded conformational epitopes of a rsgp, are present, the less likely it is to miss an infected sample due to a false negative diagnosis.

Continuous efforts have therefore been undertaken to provide larger parts of a retroviral surface glycoprotein molecule, especially of gp41 from HIV-1, in soluble form.

The biophysical as well as the biochemical properties of gp41 have been extensively studied in past years. Lu, M., et al., Nat. Struct. Biol. 2 (1995) 1075–82 have partially elucidated the trimeric structure of gp41. Since gp41 under physiological conditions forms an insoluble aggregate, the investigations were confined to truncated versions of the ectodomain gp41.

It has recently been confirmed by NMR spectroscopy (Caffrey, M., et al., J Biol Chem 275 (2000) 19877–82) that the native trimer of gp41 forms a six helix bundle comprising three parallel N-terminal central helices to which the C-terminal helices pack in an anti-parallel orientation.

High molecular aggregates of gp41 have also been described. Such aggregates most likely form by interaction of the so-called apical loop region of gp41.

By protein design, an inhibitor of HIV-1 entry into target cells has been developed by Root, M. J., et al., Science 291 (2001) 884–8. This inhibitor comprises three stretches derived from the N-terminal helical domain from the gp41 and two stretches of the C-terminal helical domain from this molecule. However, this genetically engineered construct lacks many domains and many antigenic epitopes of the native molecule, and it especially does not contain the so-called loop motif, which is known to harbor particularly immunogenic epitopes (see above).

Figure 1B:
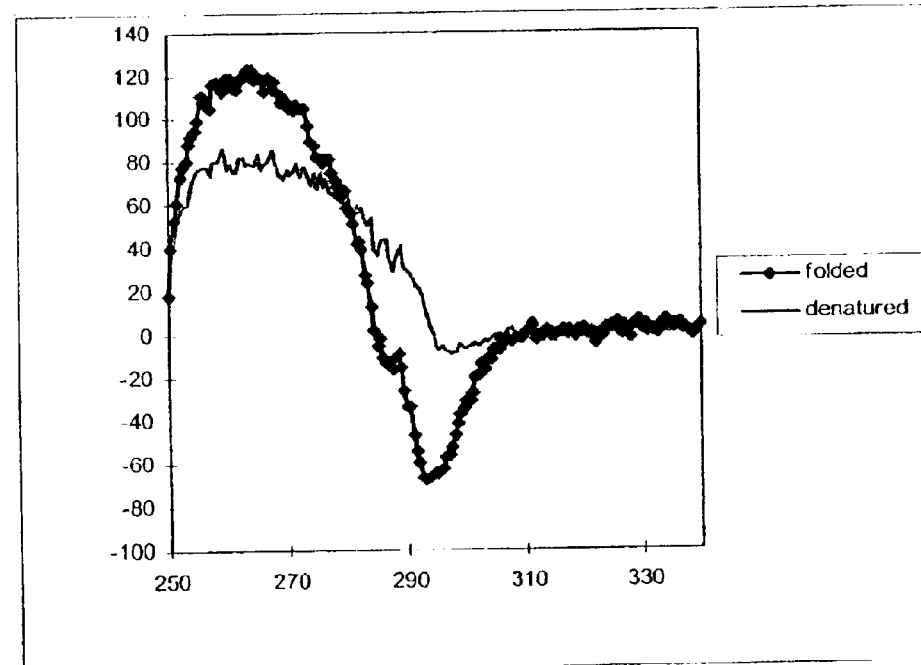

A tremendous need therefore still exists to provide as many retroviral surface glycoprotein epitopes as possible in a soluble form. Especially, there is a need for providing such soluble antigens comprising gp41 from HIV-1 or gp36 from HIV-2, respectively, for use in various therapeutic as well as diagnostic applications.

Chaperones, which are known as classical "folding helpers", are polypeptides that assist the folding and maintenance of structural integrity of other proteins. They possess the ability to promote the folding of a polypeptide both in vivo and in vitro. Generally, folding helpers are subdivided into folding catalysts and chaperones. Folding catalysts accelerate the rate limiting steps in protein folding due to their catalytic function. Examples of catalysts are further described below. Chaperones are known to bind to denatured or partially denatured polypeptides and thus help to renature proteins. Thus, unlike folding catalysts, chaperones exert a mere binding function (Buchner, J., Faseb J 10 (1996) 10–19).

Chaperones are ubiquitous stress-induced proteins involved in protein maturation, folding, translocation and degradation (Gething, M. J. and Sambrook, J., Nature 355 (1992) 33–45). Although also present under normal growth conditions, they are abundantly induced under stress conditions. This further supports the idea that their physiological function is to cope with stress conditions.

To date, several different families of chaperones are known. All these chaperones are characterized by their ability to bind unfolded or partially unfolded proteins and have a physiological function that is linked to the correct folding of proteins or the removal of denatured or aggregated protein.

Well-characterized examples of chaperones are members of so-called heat-shock families of proteins, which are designated according to their relative molecular weight; for example, hsp100, hsp90, hsp70, and hsp60, as well as the so-called shsps (small heat-shock-proteins) as described by Buchner, J., Faseb J 10 (1996) 10–19 and by Beissinger, M. and Buchner, J., Biol. Chem. 379 (1998) 245–59.

Folding catalysts, unlike chaperones, assist folding by accelerating defined rate-limiting steps, thereby reducing the concentration of aggregation-prone folding intermediates. One class of catalysts, the protein disulfide isomerases (alternatively designated as thiol-disulfide-oxido-reductases), catalyzes the formation or the rearrangement of disulfide bonds in secretory proteins. In Gram-negative bacteria, the oxidative folding of secretory proteins in the periplasm is adjusted by a cascade of protein disulfide isomerases designated DsbA, DsbB, DsbC, and DsbD (Bardwell, J. C., Mol Microbiol 14 (1994) 199–205 and Missiakas, D., et al., Embo J 14 (1995) 3415–24).

Another important class of folding catalysts referred to as peptidyl prolyl cis/trans isomerases (PPIs) comprise different members such as CypA, PpiD (Dartigalongue, C. and Raina, S., Embo J 17 (1998) 3968–80, FkpA (Danese, P. N., et al., Genes Dev 9 (1995) 387–98), trigger factor (Crooke, E. and Wickner, W., Proc Natl Acad Sci USA 84 (1987) 5216–20 and Stoller, G., et al., Embo J 14 (1995) 4939–48), and Sly D (Hottenrott, S., et al., J Biol Chem 272 (1997) 15697–701). Amongst these, FkpA, SlyD and trigger factor have been found to be related based on sequence alignments.

The peptidyl prolyl isomerase FkpA has been localized to the periplasm of Gram-negative bacteria. It has been speculated that this chaperone is important for transport and translocation of bacterial outer membrane proteins. Ramm, K. and Pluckthun, A., J Biol Chem 275 (2000) 17106–13) have shown that FkpA exhibits its beneficial effect on correct folding of proteins in two distinct ways. First, FkpA interacts with early folding intermediates, thus preventing their aggregation. Secondly, it has the ability to reactivate inactive protein, possibly also by binding to partially unfolded species that may exist in equilibrium with the aggregated form.

Some folding helpers comprise both a catalytically active domain as well as a chaperone (or polypeptide binding) domain. Representative examples are, e.g., trigger factor (Zarnt, T., et al., J Mol Biol 271 (1997) 827–37), Wang, C. C. and Tsou, C. L., Faseb J 7 (1993) 1515–7), SurA (Behrens et al., *EMBO J.*(2001) 20(1), 285–294), and DsbA (Frech, C., et al., Embo J 15 (1996) 392–98). According to our observations, the same modular structure seems to be realized in the PPIases FkpA and SlyD, respectively.

It has been demonstrated in different independent systems that an enhanced expression of chaperones may facilitate the recombinant production of a polypeptide. An example thereto can be found in WO 94/08012.

It is also known that an increased production of proteins can be achieved by using a gene construct comprising a polypeptide coding sequence as well as a chaperone sequence. This fusion concept, for example, has been shown to result in a significantly increased production of the human pro-insulin in the periplasm of *Escherichia coli* by using a gene construct comprising the human pro-insulin gene and DsbA (Winter, J., et al., Journal of Biotechnology 84 (2000) 175–185).

The approach to use chaperones for increased production of native-like folded polypeptides is mainly due to the binding and thus solubilizing function of chaperone proteins. After recombinant production of a fusion polypeptide comprising chaperone and target protein, the chaperones are customarily cleaved off from the resulting polypeptide to yield the desired polypeptide in pure form. In contrast, the present invention is based on the beneficial solubilizing effect of an appropriate chaperone while being associated with a retroviral surface glycoprotein.

BRIEF DESCRIPTION OF THE DRAWINGS

FIGS. 1A and 1B Far (1A) and Near (1B) UV CD of the HIV-1 Ectodomain gp41 (535–681)-$His_6$ Folded gp41 (thick line): buffer conditions (30 mM sodium formiate, pH 3.0) were set to induce a native-like all-helical conformation of gp41; Denatured gp41 (thin line): buffer conditions (50 mM sodium phosphate pH 3.0, 7.0 M GuHCl) were set to completely denature (unfold) gp41. Due to the high molarity of the chaotropic salt, the reference dichroitic signal in FIG. 1A (thin line) cannot be reliably monitored in the wave length region below 215 nm.

The spectra were recorded on a Jasco-720 spectropolarimeter and were averaged nine times to lower the noise. Path length was 0.2 cm for far UV CD (FIG. 1A) and 0.5 cm for near UV CD (FIG. 1B). The respective protein concentrations were 1.5 $\mu$M and 29 $\mu$M. Units of the ordinates are mean residue ellipticity and have the dimension deg×cm$^2$×dmol$^{-1}$.

Figure 2:
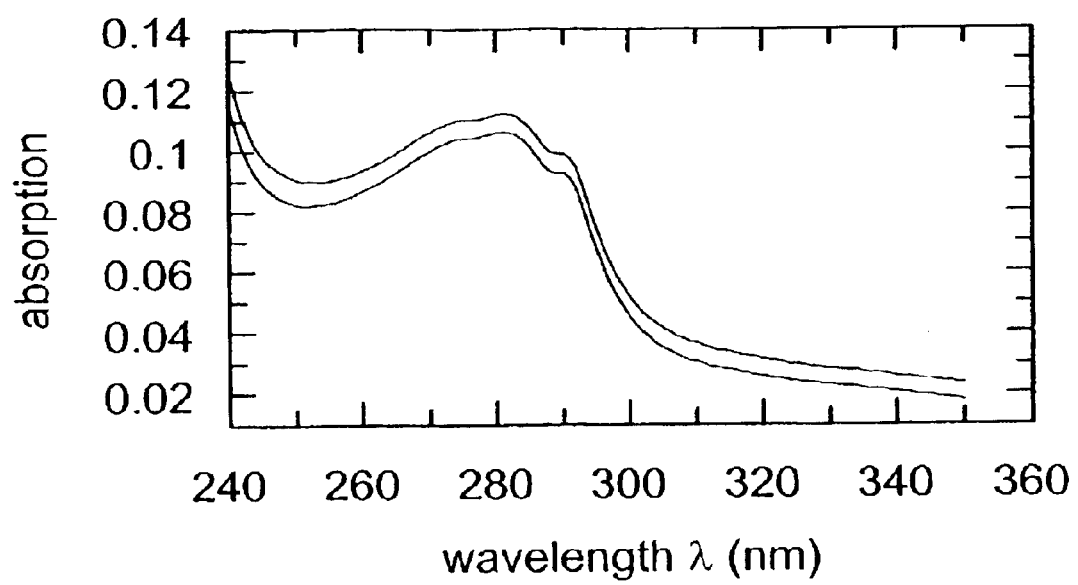

FIG. 2 Aggregation of "unchaperoned" gp41 in Physiological Buffer

Shown are UV spectra of the gp41 ectodomain one minute (lower line) and 10 minutes (upper line) after a pH jump from 3.0 to 7.5. Aggregating molecules lead to stray light effects and cause the apparent absorption beyond 310 nm. The figure is meant just to demonstrate the enormous aggregation tendency of gp41; it is noteworthy that the aggregation process does not stop at the stage indicated by the upper line.

Figure 3A:
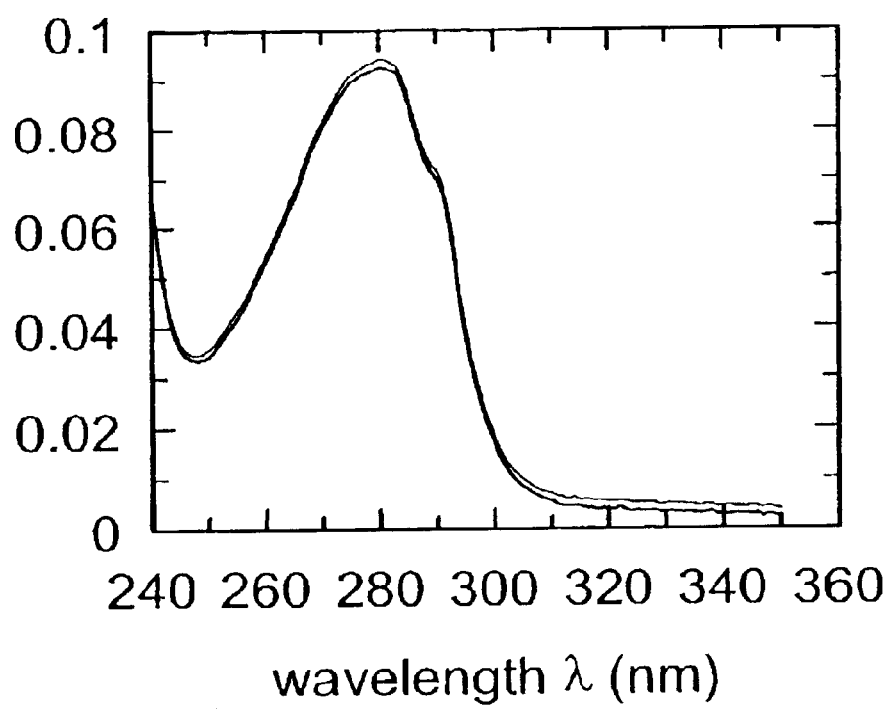
Figure 3B:
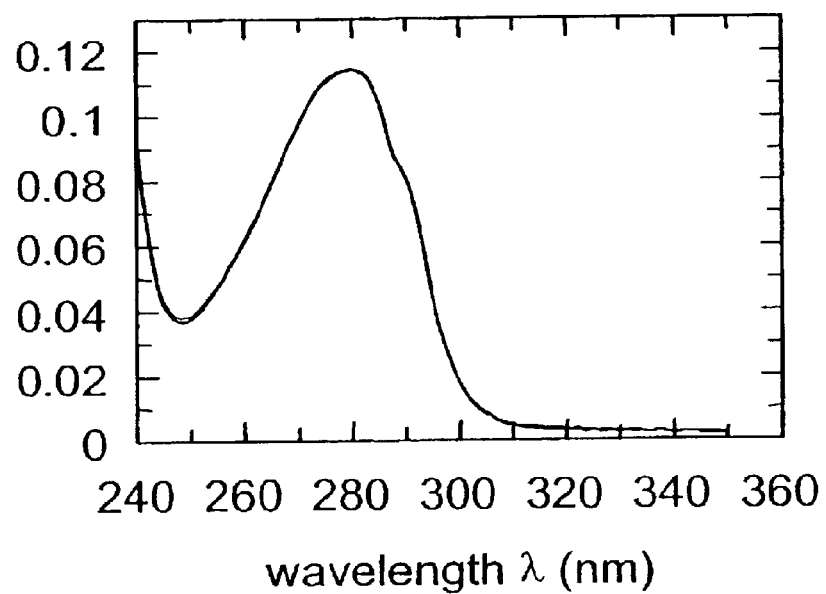

FIGS. 3A and 3B FkpA Solubilizes the gp41 Ectodomain at Neutral pH gp41 and mature FkpA were co-incubated at low pH and afterwards shifted to final buffer conditions of 20 mM sodium phosphate, pH 7.4; 50 mM NaCl, 1 mM EDTA. After 1 and 10 minutes (lower and upper line, respectively) UV spectra were recorded to assess the extent of aggregation in the samples. FIG. 3A shows the suppression of aggregation by a two-fold molar excess of the chaperone, FIG. 3B shows the effect of a four-fold excess. The final concentration of gp41 was about 1 $\mu$M. Since stray light (leading to an apparent absorption beyond 300 nm) was reduced to a minimum, there is compelling spectroscopic evidence that FkpA efficiently solubilizes the gp41 ectodomain in a dose-dependent fashion.

Figure 4:
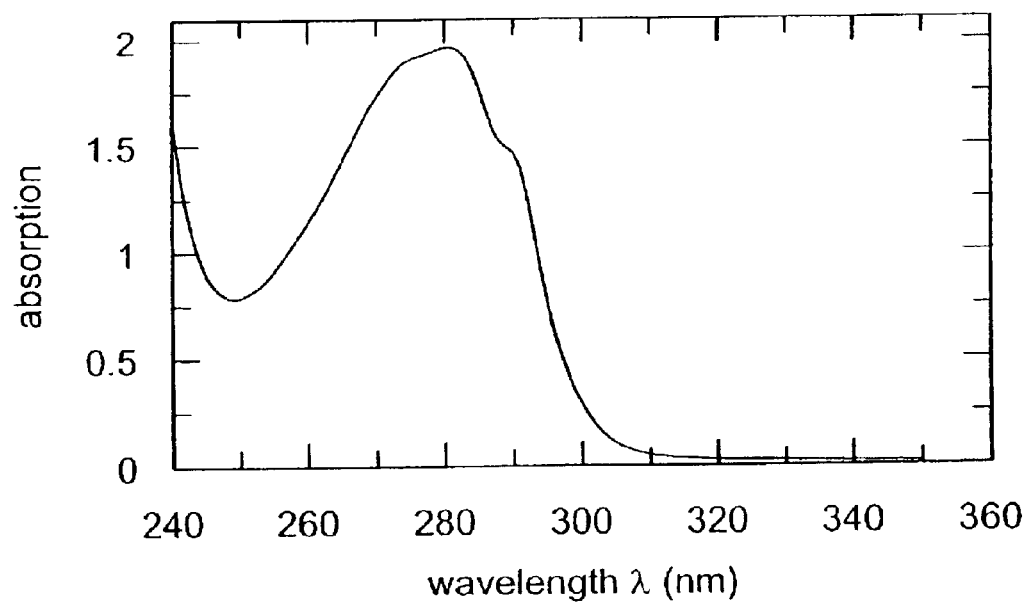

FIG. 4 UV Spectrum of FkpA-gp41 at pH 2.5

UV-spectrum of the fusion polypeptide FkpA-gp41 after dialysis against 50 mM sodium phosphate, pH 2.5; 50 mM NaCl. Surprisingly, the two-domain construct remains completely soluble after removal of the solubilizing chaotropic agent GuHCl. There is no evidence for the existence of light-straying aggregates that would be expected to cause a baseline drift and significant apparent absorption at wavelengths beyond 300 nm.

Figure 5:
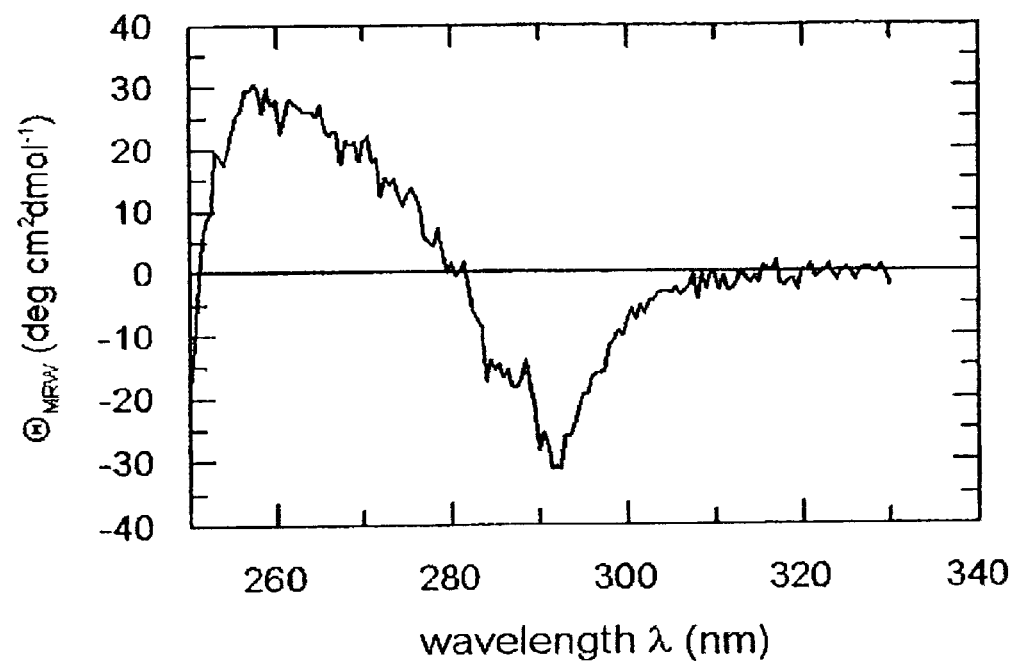

FIG. 5 Near UV CD Spectrum of FkpA-gp41 at pH 2.5

The spectrum was recorded on a Jasco 720 spectropolarimeter in 20 mM sodium phosphate, pH 2.5; 50 mM NaCl at 20° C. and was accumulated nine times to lower the noise. Protein concentration was 22.5 $\mu$M at a path length of 0.5 cm. The aromatic ellipticity shows the typical signature of gp41 (for reference see FIG. 1B). At pH 2.5, FkpA is largely unstructured and does not contribute to the signal in the Near-UV-CD at all.

Figure 6:
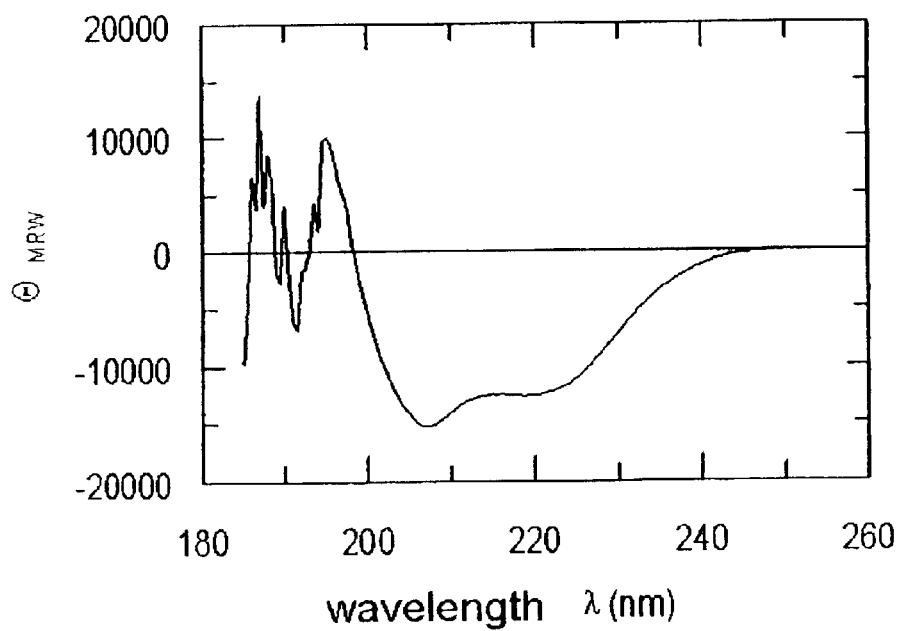

FIG. 6 Far UV CD Spectrum of FkpA-gp41 at pH 2.5

The spectrum was recorded on a Jasco 720 spectropolarimeter in 20 mM sodium phosphate pH 2.5; 50 mM NaCl at 20° C. and was accumulated nine times to improve the signal-to-noise ratio. Protein concentration was 2.25 $\mu$M at a path-length of 0.2 cm. The minima at 220 and 208 nm point to a largely helical structure of gp41 in the context of the fusion protein. The spectral noise below 197 nm is due to the high amide absorption and does not report on any structural features of the fusion protein. Nevertheless, the typical helix-maximum at 193 nm can be guessed.

Figure 7:
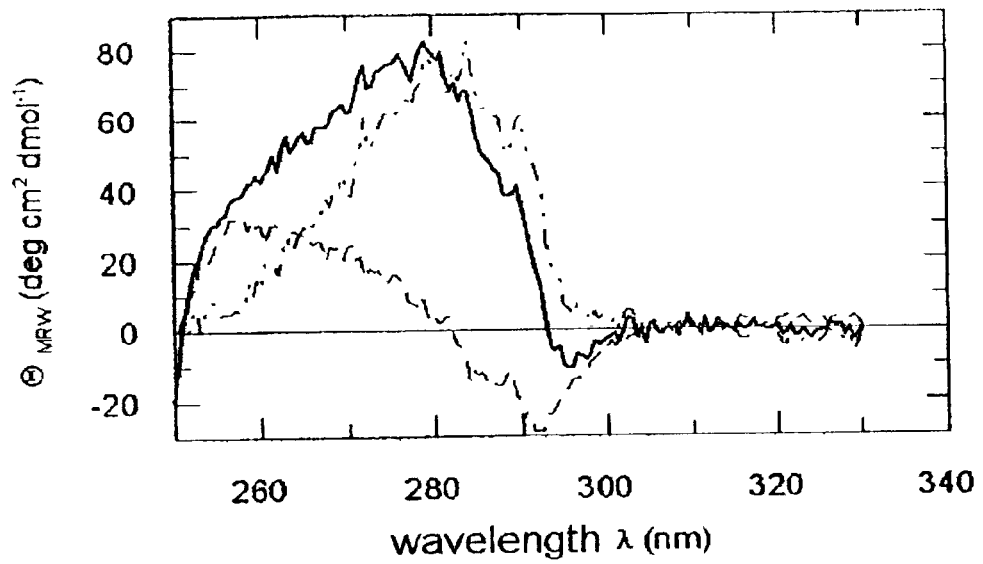

FIG. 7 Near UV CD of FkpA-gp41 Under Physiological Buffer Conditions

The spectrum was recorded on a Jasco 720 spectropolarimeter in 20 mM sodium phosphate, pH 7.4; 50 mM NaCl at 20° C. and was accumulated nine times to lower the noise. Protein concentration was 15.5 $\mu$M at a path-length of 0.5 cm. Strikingly, the aromatic ellipticity of the covalently linked protein domains of g41 and FkpA (continuous line) is made up additively from the contributions of native-like all-helical gp41 at pH 3.0 (lower dashed line) and the contributions of FkpA at pH 7.4 (upper dashed line). This indicates that the carrier FkpA and the target gp41 (i.e. two distinct functional folding units) refold reversibly and quasi-independently when linked in a polypeptide fusion protein.

Figure 8:
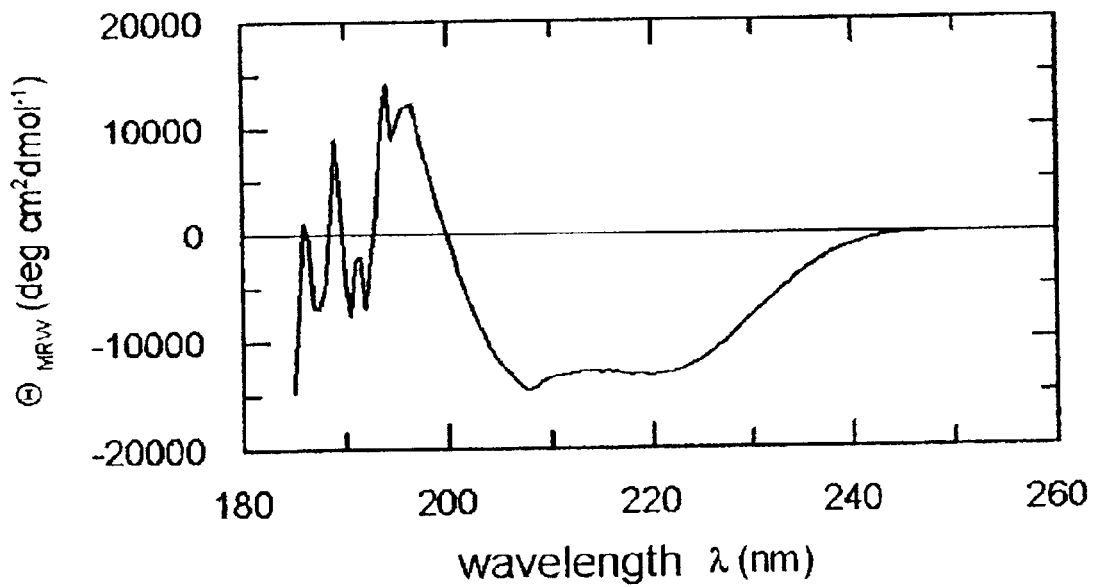

FIG. 8 Far UV CD of FkpA-gp41 Under Physiological Buffer Conditions

The spectrum was recorded on a Jasco 720 spectropolarimeter in 20 mM Sodium phosphate, pH 7.4; 50 mM NaCl at 20° C. and accumulated nine times to improve the signal-to-noise ratio. Protein concentration was 1.55 $\mu$M at a path-length of 0.2 cm. The strong signals at 222 nm and 208 nm, respectively, point to a largely helical structure of gp41 in the context of the fusion construct. The noise below 198 nm is due to the high protein absorption and does not reflect any secondary structural properties of FkpA-gp41.

Figure 9:
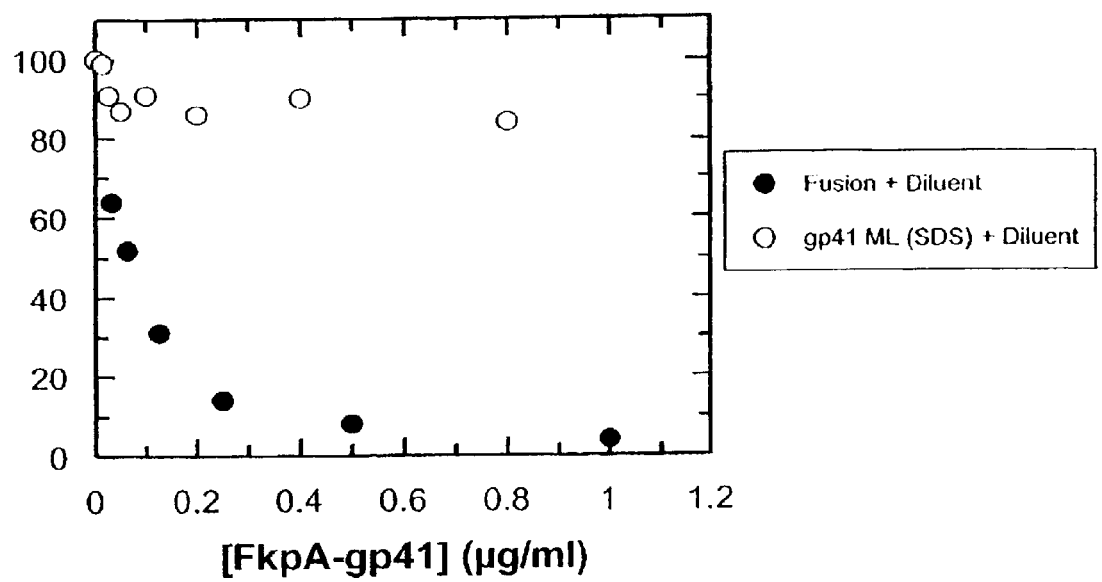

FIG. 9 FkpA-linked gp41 is Both Soluble and Highly Immunoreactive in an HIV-assay FkpA-gp41 is a strong competitor in the COBAS CORE HIV Combi assay. Shown is the inhibitory potential of the soluble FkpA-gp41 polypeptide (filled circles) after pretreatment with diluent buffer (containing Triton X-100 as a helper detergent) in comparison to the gp41 ectodomain alone (empty circles). It is evident that the gp41 ectodomain (within the intramolecular complex of the fusion protein) retains its high immunoreactivity even in the presence of detergent, whereas the naked ectodomain almost completely loses immunoreactivity. The HIV-positive serum tested was internal serum number 21284 in a dilution of 1:3000.

Figure 10:
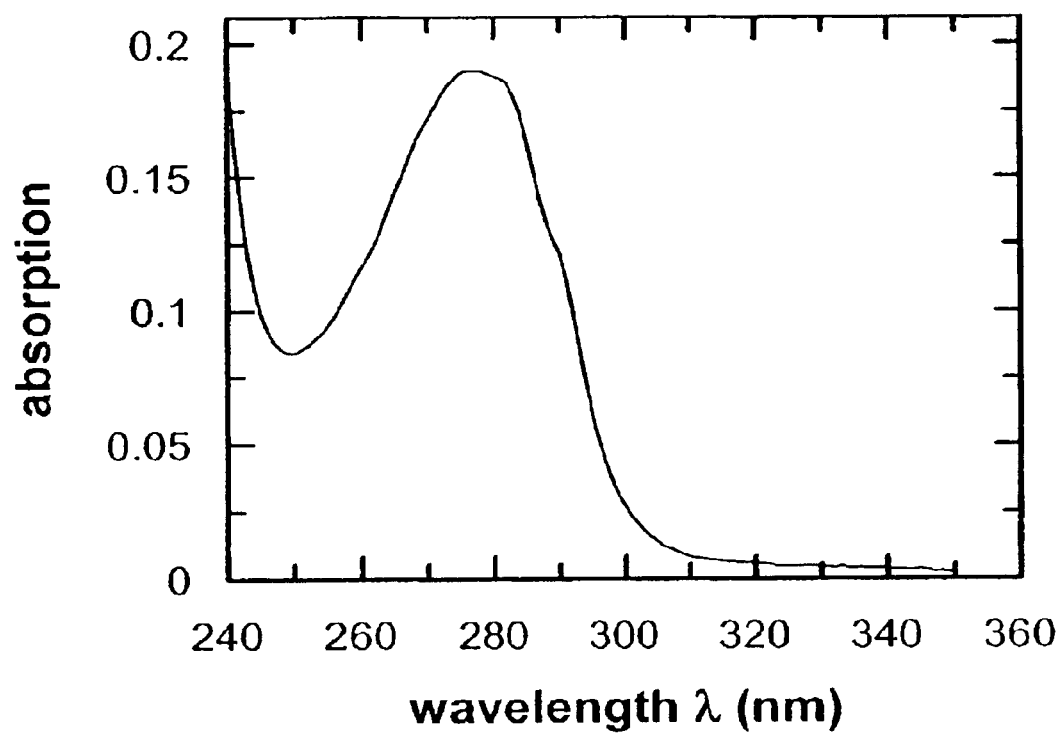

FIG. 10 UV-spectrum of FF36 After Renaturing Gel Filtration

The spectrum provides compelling evidence that the gp36 fusion peptide is soluble and does not aggregate when refolded on a Sux 200 column according to the renaturing gel filtration method as described in the Examples section.

Figure 11A:
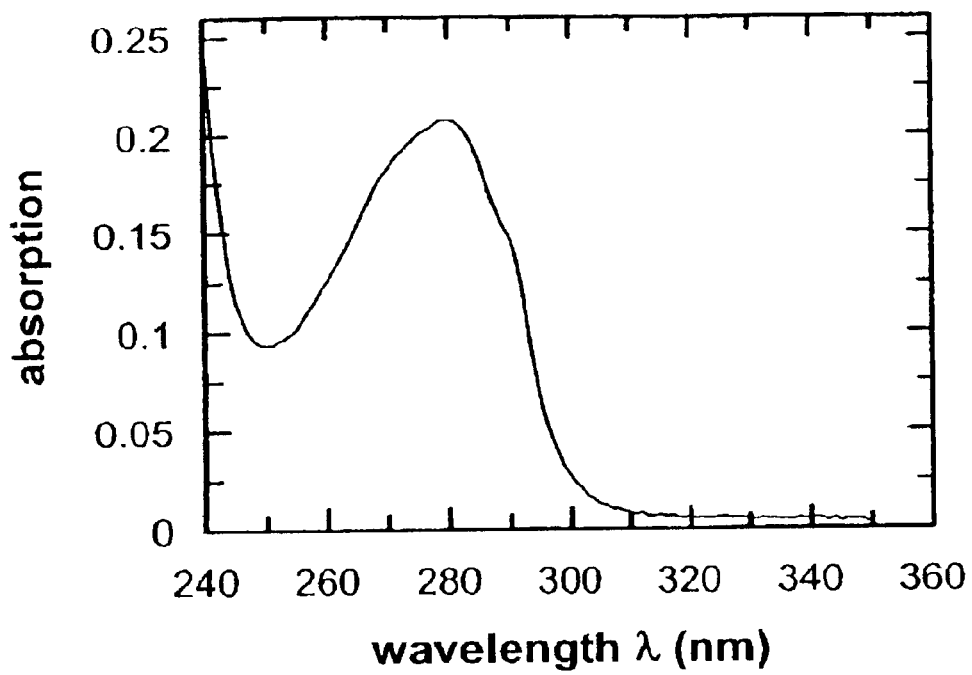
Figure 11B:
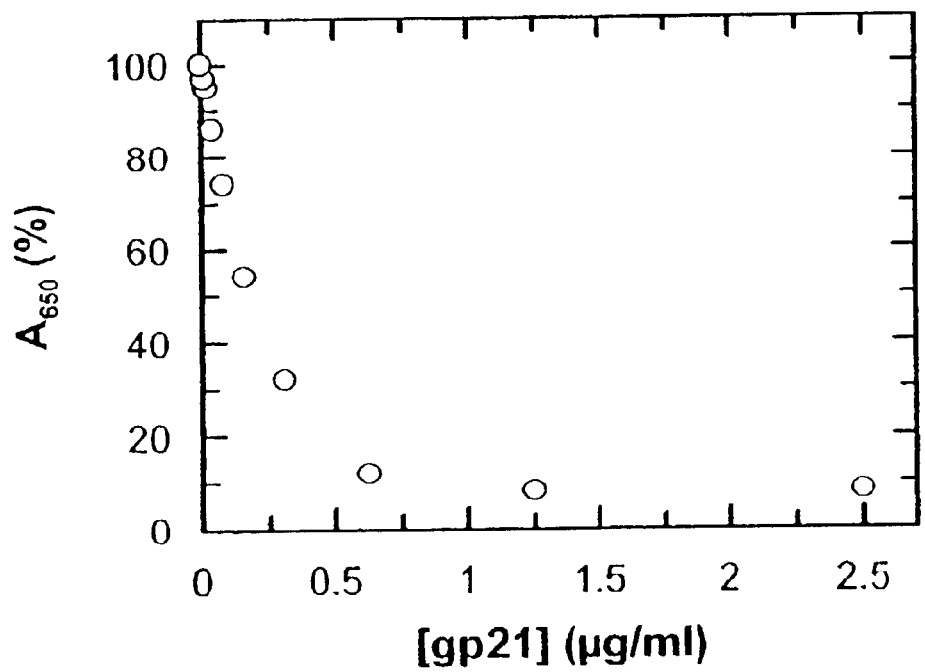

FIGS. 11A and 11B FkpA-gp21 is Both a Soluble and an Immunologically Reactive Fusion Polypeptide After renaturing gel filtration, the refolded FkpA-gp21 fusion protein elutes highly soluble and shows no aggregation tendency in the UV-spectrum (FIG. 11A). When assessed in a competitive-type immunoassay experiment in the COBAS CORE with HTLV-positive serum 858893-00 (1:10 dilution), FkpA-gp21 turns out to possess excellent immunological properties (FIG. 11B).

DETAILED DESCRIPTION

The present invention relates to a method of producing a soluble complex comprising a target protein which is essentially insoluble and a peptidyl-prolyl-isomerase class chaperone comprising mixing said protein and said chaperone in a buffer wherein both, the protein and the chaperone are solubilized and adjusting the buffer to physiological conditions wherein the protein-chaperone complex formed is soluble.

It was a task of the present invention to investigate whether it is possible to provide more retroviral surface glycoprotein epitopes or even the e-gp41 molecule or the e-gp36, respectively, in soluble form.

A further task of the present invention was to investigate whether it is possible to provide variants of gp41 and or gp36, respectively, which are more easy to handle and/or which, especially under buffer conditions as required for performing an immunoassay or as required for immunization, are soluble in form of a complex comprising the variant and a chaperone of the peptidyl-prolyl-isomerase class of chaperones.

To our surprise, we found that folding helpers, e.g., many members of the peptidyl prolyl isomerase (PPI) class, especially from the FKBP family, not only exhibit catalytic activity, but also bring about drastic beneficial effects on solubility of amyloidogenic proteins, or more generally speaking, of proteins tending to aggregation. They do so by forming soluble complexes with such proteins that are otherwise (i.e. in an unchaperoned, isolated form) prone to aggregation. Such proteins that are otherwise hardly soluble or insoluble under physiological conditions turn out to be soluble under mild physiological conditions (i.e. without need for solubilizing additives such as detergents or chaotropic agents) once they are bound in a complex with the appropriate PPI chaperone. Thus, we were able to produce, for example, soluble protein-chaperone complexes comprising, e.g., the gp41 protein of HIV-1 as an aggregation prone target protein and FkpA or other FKBPs as solubility-confering chaperones.

In addition, we have found that certain well defined variants of HIV-1 gp41 or of HIV-2 gp36, respectively, are especially suited to form a soluble complex with chaperones of the PPI-class.

The complexes of gp41 and FkpA or of gp36 and FkpA, for example, are readily soluble, e.g., under physiological conditions, they can be easily labeled in convenient pH ranges, and they can be used to great advantage in the detection of antibodies against gp41 or gp36, respectively, of HIV (1 or 2, respectively) and therefore in the diagnosis of an HIV infection.

A "target protein" according to the present invention may be any protein which is essentially insoluble in an aqueous buffer solution with pH 7.4 consisting of 20 mM sodium phosphate and 150 mM sodium chloride. Preferred target proteins for example are amyloidogenic proteins, surface glycoproteins of amyloidogenic viruses, retroviral surface glycoproteins, especially HIV-1 gp41, HIV-2 gp36 and HTLV gp21.

One important group of target polypeptides are the so-called amyloidogenic proteins or polypeptides. Such amyloidogenic proteins have been found in aggregated form in bodily fluids or compartments. Well-known examples are serum amyloid A (sAA), the so-called β-A4 or Aβ (a polypeptide of 42 or 43 amino acids known to form the characteristic amyloid deposits in brains of Alzheimer's Disease), the so-called prion proteins (the $PrP^{Sc}$ form accumulates in aggregates in BSE or Creutzfeldt-Jacob disease), and retroviral surface glycoproteins, like HIV-1 gp41, which is found in amyloid-like plaques in the brain of patients suffering from HAD (HIV associated dementia). In a preferred embodiment, a chaperone, preferably a PPI chaperone, is used to form a soluble complex comprising an amyloidogenic protein and the chaperone. To great advantage such a complex can be used in many different immunoassay procedures. Preferably such a complex is used in an immunoassay according to the double antigen bridge concept.

HIV and other enveloped viruses, such as HTLV, influenza virus and Ebola virus, all express surface glycoproteins that mediate both cell attachment and membrane fusion. To serve these functions, all these surface glycoproteins contain extremely hydrophobic segments rendering them difficult to handle in vitro, prone to aggregation, and making them challenging targets for in vitro refolding attempts. In a further preferred embodiment, the present invention relates to a soluble complex comprising a PPI chaperone and a surface glycoprotein of an enveloped virus. It especially relates to the use of a complex comprising a PPI chaperone and a surface glycoprotein of an enveloped virus in an immunoassay for the detection of antibodies to the surface glycoprotein.

HAD is a well-known complication of HIV infection. As described by Caffrey, M., et al. supra, with respect to histological phenomenology, HAD is very similar to the spongiform encephalopathy called Creutzfeldt-Jacob disease. The etiology of Creutzfeldt-Jacob disease is generally considered to arise from the amyloidgenic accumulation of plaques comprising a modified prion protein (Prusiner, S. B., Proc Natl Acad Sci USA 95 (1998) 13363–83). An analogous pathogenesis for HAD involving high molecular weight aggregates of e-gp41 is very likely. It is noteworthy that the neurological lesions in HIV encephalopathy share pathological and radiological features with Binswanger's disease.

Preferred amyloidogenic proteins according to the present invention are gp41 derived from HIV-1, gp36 derived from HIV-2, or gp21 derived from HTLV, respectively.

A protein is considered "essentially insoluble" if in a buffer consisting of 20 mM sodium phosphate pH 7.4, 150 mM NaCl it is soluble in a concentration of 50 nM or less.

A complex according to the present invention comprising a PPI-chaperone and a target protein is considered "soluble" if under physiological buffer conditions, e. g. in a buffer consisting of 20 mM sodium phosphate pH 7.4, 150 mM NaCl the target protein comprised in the PPI-chaperone complex is soluble in a concentration of 100 nM or more.

We developed a method comprising the steps of mixing the target protein and the chaperone in a buffer wherein both, the protein and the chaperone are solubilized and adjusting the buffer to physiological conditions wherein the protein-chaperone complex formed remains soluble.

Production of the soluble chaperone-target protein complex starts from a solubilizing buffer condition, i.e., from a buffer wherein both, the target protein and the chaperone are soluble. An appropriate buffer, which may be termed "non-physiological" "solubilizing" buffer has to meet the requirement that both the target protein and the PPI chaperone are not denatured or at least not irreversibly denatured. Starting from such buffer conditions, the chaperone binds to the target protein, and a change of the buffer conditions from non-physiological to physiological conditions is possible without precipitation of the target protein.

An appropriate (non-physiological) buffer, i.e., a buffer wherein both the target protein which is essentially insoluble and the PPI-chaperone are soluble either makes use of high or low pH, or of a high chaotropic salt concentration or of a combination thereof.

In case of the production of an intermolecular complex comprising a PPI-chaperone and a target protein which is essentially insoluble the non-physiological buffer preferably is a buffer with rather a high or rather a low pH. Preferably such buffer has a pH of 9 to 12 in the high pH-range or of 2 to 4.5 in the low pH-range.

In case of the production of an intramolecular complex comprising a PPI-chaperone and a target protein which is essentially insoluble the solubilizing buffer preferably is a buffer with rather a high concentration of a chaotropic salt, e.g. 6.0 M guanidinium chloride at a pH of about 6. Upon renaturation the target protein assumes its native-like structure and the intramolcular complex forms.

In the context of this invention physiological buffer conditions are defined by a pH value between 5.0 and 8.5 and a total salt concentration below 500 mM, irrespective of other non-salt ingredients that optionally may be present in the buffer (e.g. sugars, alcohols, detergents) as long as such additives do not impair the solubility of the complex comprising the target protein and the chaperone.

In a further preferred embodiment the present invention relates to a method of producing a soluble retroviral surface glycoprotein-chaperone complex comprising: mixing a retroviral surface glycoprotein and a peptidyl prolyl isomerase in a buffer wherein both the retroviral surface glycoprotein and the peptidyl prolyl isomerase are solubilized and form a complex, and adjusting the buffer to physiological conditions wherein the complex is soluble.

The term "retroviral surface glycoprotein" or "rsgp" as used in the present invention shall comprise gp41 of HIV-1 and gp36 of HIV-2, as well as corresponding envelope glycoproteins derived from other mammalian immunodeficiency viruses. Preferred retroviral surface glycoproteins are gp41 from HIV-1, gp36 from HIV-2 and gp21 of HTLV. Especially preferred rsgps are gp41 of HIV-1 and gp36 of HIV-2. The term rsgp as outlined here does also comprise naturally occurring as well as synthetically engineered variants of a rsgp.

It has been found that certain well-defined substitutions of amino acids within the N-helical domain of gp41 or gp36, respectively, bring about further advantages in the overall properties of these molecules as compared to polypeptides having the wild-type sequence of gp41 or gp39, respectively. These variants represent a preferred embodiment according to the present invention. Especially a variant of HIV-1 gp41 comprising at least one amino acid substitution and at most four amino acid substitutions at one or more positions selected from the group of positions Leu 555, Leu 566, Ile 573, and Ile 580, wherein these positions are the positions known from the HIV-1 gp41 wild-type sequence (SEQ ID NO:1) or correspond to the positions known therefrom, characterized in that the substitution amino acid is or, respectively and independently, are selected from the group consisting of serine, threonine, asparagine, glutamine, aspartic acid and glutamic acid, or a variant of HIV-2 gp36 comprising at least one amino acid substitution and at most three amino acid substitutions at a position selected from the group of positions Leu 554, Leu 565, and Val 579, wherein these positions are the positions known from the HIV-2 gp36 wild-type sequence (SEQ ID NO:2) or correspond to the positions known therefrom, characterized in that the substitution amino acid is or, respectively and independently, are selected from the group consisting of serine, threonine, asparagine, glutamine, aspartic acid and glutamic acid, is appropriate to at least partially solve the problems known from the art.

The novel variants of gp41 or gp36, respectively, are less prone to aggregation, better soluble and more easy to handle as compared to their corresponding polypeptides of the wild-type sequences. The improved solubility becomes especially evident once attempts are made to provide for a reagent which under physiological buffer conditions comprises gp41 or gp36 in soluble form. It has proven especially advantageous to combine the favorable properties of the novel variants with the effects rendered by a chaperone selected from the petidyl-prolyl-isomerase (PPI) class of chaperones. Therefore the invention further relates to the use of a variant of gp41 and/or a variant of gp36 as described in the present invention in the production of a soluble complex comprising said variant and a chaperone of the peptidyle-prolyl-isomerase class of chaperones.

A soluble complex comprising a variant HIV-glycoprotein and a PPI-class chaperone is preferably obtained from a single recombinant protein comprising both a variant HIV gp41 or HIV-2 gp36, respectively and a PPI class chaperone. Thus a preferred embodiment is a recombinant protein comprising a variant of HIV-1 gp41 or HIV-2 gp36 as described in the present invention and a chaperone selected from the peptidyle-prolyl-isomerase class of chaperones.

The fact that the novel variants of gp41 or gp36 are more easy to handle as the wild-type polypeptides renders them ideal for various purposes like use as an immunogen or use as an antigen. In a preferred embodiment the present invention is directed to the use of a variant of gp41 and/or of gp36 according to the present invention or of a complex comprising a PPI chaperone and such variant, e.g., as a single recombinant protein, in an immunoassay. Most intriguingly, a fusion protein comprising both a retroviral surface glycoprotein and a PPI chaperone can be solubilized and renatured under appropriate conditions and has been found to form a soluble intramolecular rsgp-chaperone complex that enables convenient labeling and reliable detection in an HIV-immunoassay.

The soluble complex between a retroviral surface glycoprotein and a chaperone can be used to great advantage in an immunoassay for detection of antibodies according to the double antigen bridge concept.

An rsgp-chaperone complex comprising gp41 from HIV-1 or gp36 from HIV-2 is especially advantageous in the detection of antibodies against HIV in an early phase of infection. With a soluble chaperone-gp41 complex or a soluble chaperone-gp36 complex, it is possible to perform an immunoassay, preferably according to the bridge concept, which allows for sensitive and early detection of antibodies against HIV in a bodily fluid sample.

The fact that chaperones can form complexes with otherwise insoluble proteins can also be used with great advantage in order to more generally improve immunoassays, preferably immunoassays according to the bridge concept. The bridge concept allows for the use of a chaperone-antigen complex as a first antigen (mostly a so-called capturing antigen on the solid phase side) and a second chaperone-antigen complex (mostly a detection antigen on the detection side). In order to minimize background reaction problems caused by binding of chaperone-reactive antibodies, such bridge assays can further be advantageously modified by making use of a first chaperone for the solid phase side and a second chaperone for the detection side derived from different species.

It is now possible to perform immunoassays according to the bridge concept employing a labeled chaperone-antigen complex. It is also possible to produce a chaperone-antigen complex wherein solely the chaperone is labeled, making sure that the antigen is not modified or negatively influenced (e.g. in terms of conformation) by such labeling.

The mode and strategy of chemical coupling can be selected as required. In case of polypeptides, coupling chemistries targeting —SH, —$NH_2$ or —$COO^-$ residues as well as the —OH group of tyrosines, the imidazol group of histidines, or the heterocyclic imino groups of tryptophanes are at hand. Several appropriate coupling chemistries are known for each of these functional groups (Aslam, M. and Dent, A., supra). Routine protein coupling chemistries require a protein to be soluble under the working buffer conditions, e.g., within a pH range of about 5 to 8.5. As, e.g., gp41 is not soluble in this pH range unless denatured, e.g., by SDS, native-like folded gp41 has hitherto not been amenable to chemical coupling. The gp41-chaperone complexes we describe here provide a convenient means to produce soluble labeled HIV-envelope proteins for immunoassays irrespective of the detection format used.

In a preferred embodiment, the present invention relates to the process for the production of a soluble rsgp-chaperone complex comprising the steps of mixing a solubilized retroviral surface glycoprotein and a chaperone selected from the peptidyl prolyl isomerase class under non-physiological buffer conditions and thereafter adjusting the buffer to physiological conditions thus forming an intermolecular complex.

A chaperone and a retroviral surface glycoprotein can not only be used as separate polypeptides. We surprisingly have observed that it is advantageous to link both proteins covalently. Such covalent linkage is possible by conventional chemical cross-linking procedures; preferably, however, the covalent linkage is achieved by producing a recombinant polypeptide comprising a retroviral surface glycoprotein and a chaperone.

In a further preferred embodiment, the present invention relates to a process for the production of a soluble rsgp-chaperone complex comprising the steps of solubilizing, under appropriate buffer conditions, a protein comprising a covalently linked retroviral surface glycoprotein and a chaperone protein selected from the peptidyl prolyl isomerase class and thereafter adjusting the buffer to physiological conditions. This way an intramolecular complex is obtained.

The present invention teaches the use of chaperones derived from the class of folding helpers termed peptidyl prolyl cis/trans isomerases (PPIs) (cf. Dartigalongue, C. and Raina, supra). Well-known examples of this family are members called CypA, PpiD (Dartigalongue, C. and Raina, S., Embo J 17 (1998) 3968–80; Schmid, F. X., Molecular chaperones in the life cyle of proteins (1998) 361–389, Eds. A. L. Fink and Y. Goto, Marcel Decker In., New York), FkpA (Danese, P. N., et al., Genes Dev 9 (1995) 387–98) and trigger factor (Crooke, E. and Wickner, W., Proc Natl Acad Sci USA 84 (1987) 5216–20; Stoller, G., et al., Embo J 14 (1995) 4939–48).

The peptidyl prolyl isomerases are subdivided into three families, the parvulines (Schmid, F. X., supra, Rahfeld, J. U., et al., FEBS Lett 352 (1994) 180–4) the cyclophilines (Fischer, G., et al., Nature 337 (1989) 476–8, and the FKBP family (Lane, W. S., et al., J Protein Chem 10 (1991) 151–60). The FKBP family exhibits an interesting biochemical feature since its members have originally been identified by their ability to bind to macrolides, e.g., FK 506 and rapamycin (Kay, J. E., Biochem J 314 (1996) 361–85).

Prolyl isomerases may comprise different subunits or modules of different function, e.g., a module exhibiting catalytic activity and a module exhibiting the chaperone or binding activity. Such modular members of the FKBP family are FkpA (Ramm, K. and Pluckthun, A., J Biol Chem 275 (2000) 17106–13), SlyD (Hottenrott, S., et al., J Biol Chem 272 (1997) 15697–701) and trigger factor (Scholz, C., et al., Embo J 16 (1997) 54–8). In a preferred embodiment the invention relates to a soluble complex comprising a retroviral surface glycoprotein and a chaperone selected from the peptidyl prolyl isomerase class of folding catalysts.

Of course, the present invention is not restricted to the use of the specifically mentioned members of the peptidyl prolyl isomerase class, but can also be performed using chaperones stemming from the same class but derived from a different species of bacteria. Preferably members of the FKBP family of the PPI class of chaperones are used.

In a further embodiment, it is preferred to use homologues derived from eucaryotic organisms, and it is very preferred to use PPIases from human origin because these PPIases should not be recognized by antibodies from human sera and thus should not interfere in serological assays (i.e. assays based on the detection of human antibodies).

It is also well known and appreciated that it is not necessary to always use the complete sequence of a molecular chaperone. Functional fragments of chaperones (so-called modules) which still possess the required abilities and functions may also be used (cf. WO 98/13496).

For instance, FkpA is a periplasmic PPI that is synthesized as an inactive precursor molecule in the bacterial cytosol and translocated across the cytoplasmic membrane. The active form of FkpA (mature FkpA or periplasmic FkpA) lacks the signal sequence (amino acids 1 to 25) and thus comprises amino acids 26 to 270 of the precursor molecule. Relevant sequence information relating to FkpA can easily be obtained from public databases, e.g., from "SWISS-PROT" under accession number P 45523.

A close relative of FkpA, namely SlyD, consists of a structured N-terminal domain responsible for catalytic and chaperone functions and of a largely unstructured C-terminus that is exceptionally rich in histidine and cysteine residues (Hottenrott, S., et al., J Biol Chem 272 (1997) 15697–701). We found that a C-terminal truncated variant of SlyD comprising amino acids 1–165 efficiently exerts its solubilizing functions on gp41 and gp36. Unlike in the wild-type SlyD, the danger of compromising disulfide shuffling is successfully circumvented in the truncated SlyD-variant (1–165) used.

Variants of the above-discussed chaperones, bearing one or several amino acid substitutions or deletions, may also be used to perform a process according to the present invention.

Appropriate chaperones from alternative sources, and appropriate fragments or mutants of chaperones, can be easily selected by using the procedures as described in the Examples. They can be used either in free form or covalently linked to a retroviral surface glycoprotein in order to produce a soluble rsgp-chaperone complex. In a preferred embodiment according to the present invention, a binding-competent PPIase chaperone is recombinantly linked to a retroviral surface glycoprotein to yield high expression of the gene product in the bacterial cytosol. A binding-competent PPIase as referred to in the present invention encompasses at least the functional unit that mediates binding to extended polypeptide substrates (i.e. the substrate binding or chaperone motif), irrespective of its catalytic PPIase activity.

We have also observed that some chaperones not belonging to the PPI class of folding catalysts can form a soluble complex with a retroviral surface glycoprotein. A further preferred embodiment according to the present invention therefore is a soluble complex between Skp (also known as OmpH; Missiakas, D., et al., Mol Microbiol 21 (1996) 871–84) and a retroviral surface glycoprotein. Yet a further preferred embodiment is a soluble complex comprising a retroviral surface glycoprotein and GroEL or parts thereof. Chaperones which are homologous to Skp may also be used.

It is known (e.g., Scholz et al., supra) that modular PPIs preferentially bind to denatured or partially denatured proteins. PPIases have now been found to have the striking property of not only catalyzing the folding of proteins, but also of forming stable complexes with such proteins, thereby confering solubility. Surprisingly the PPIases studied (such as TF, SlyD and FkpA) bind to and thus, e.g., solubilize native-like folded retroviral surface glycoprotein. "Native-like" or "native-like folded" gp41, according to the present invention, is characterized both by a high helical content in secondary structure as assessed by Far-UV-CD and by tertiary contacts as assessed by Near-UV-CD, which are reflected in the typical "gp41-signature" as shown in FIGS. 1B and 5, respectively. Furthermore, the UV-spectrum of "native-like" gp41, according to the present invention, does not show significant absorption at wavelengths higher than 320 nm (which would point to light-straying particles such as aggregates).

There is a wealth of information on complex formation between model biomolecules, e.g., between an antibody and an antigen (for review see Braden, B. C. and Poljak, R. J., Faseb J 9 (1995) 9–16). Usually, complex formation and dissociation occur in parallel, the complex and the binding partners coexist in free equilibrium. Likewise, the same seems true for complexes between PPI chaperones and amyloidogenic proteins as described in the present invention.

The formation of a complex, as described in the present invention, is an especially important property because complexes between the PPI chaperone and a protein which is essentially insoluble, e.g., under physiological buffer conditions have been found to be readily soluble, e.g., under physiological buffer conditions. Antigens which are soluble under physiological conditions are of tremendous advantage in diagnostic applications. They can be directly used, e.g., as standard material. Furthermore, they can be conjugated to appropriate markers or to appropriate binding groups.

As discussed above, gp36 from HIV-2 serves similar functions (i.e., membrane fusion and virus entry) and is of similar diagnostic relevance as gp41 from HIV-1. Many technical problems are discussed in this application using gp41 of HIV-1 as a prototypical example of a retroviral surface glycoprotein. Only for the sake of clarity, the discussion and description predominantly focuses on gp41 of HIV-1. However, similar considerations apply for other retroviral surface glycoproteins, especially for gp36 from HIV-2 and for gp21 from HTLV.

It is known that naturally occurring isolates of HIV-1 or HIV-2 may comprise variants of the originally isolated and described amino acid sequences. Such naturally occurring as well as synthetically engineered variants of mammalian immunodeficiency rsgps are also within the scope of the present invention.

The present invention in a preferred embodiment relates to variants of the rsgp or transmembrane glycoprotein of the human immunodeficiency virus (HIV). Variants comprising specific amino acid substitutions in the N-helical domain of HIV-1 gp41 or of HIV-2 gp36, are disclosed.

The amino acid positions of both the N-helical as well as the C-helical domains involved in helix-to-helix contact are known from the literature for HIV-1 gp41 and can be extrapolated to the HIV-2 homologue gp36. It has been found that mutating these positions influences the properties of gp41 or gp36, respectively, especially in the context of a fusion protein comprising this variant and a PPI-chaperone domain.

The "a" and "d" amino acid positions in the helical wheel projection of the gp41 leucine zipper are preferred targets to create a variant according to the present invention. Amino acid residues in the "a" position (numbering according to Chan, D. C., et al., Cell 89 (1997) 263–73) are Q552, I559, L566, I573 and I580; the respective "d" positions are I548, L555, Q562, T569 and L576.

In order to improve solubility without compromising the helical integrity of the zipper motif, it is preferred that the mutation positions are separated from each other by more than one helical turn. This prerequisite is met, e.g., by substitution of the consecutive "a"-residues Q552, I559, L566 and I573 as well as, e.g., by substitution of the consecutive "d"-residues I548, L555, Q562 and T569. In other words, the mutated residues are separated from each other by at least 6 wild-type amino acid residues, thus following exactly the heptad motif. It is also possible to mutate both "a" and "d" residues within a variant under the aforementioned condition that substitution positions are separated from each other by more than one helical turn.

Likewise, alterations in the gp36 ectodomain of HIV-2 were surprisingly found to yield a readily soluble recombinant protein when fused to SlyD or FkpA. Here, the "a" positions are Q551, V558, L565, T572, V579, and the "d" positions are I547, L554, Q561, T568 and L575.

Preferably, 1 to 6 amino acids selected from the group of positions comprising the positions Q552, I559, L566, I573, I580, I548, L555, Q562, T569, and L576 of HIV-1 gp41 or Q551, V558, L565, T572, V579, I547, L554, Q561, T568, and L575 of HIV-2 gp36, respectively, are substituted by a smaller or more hydrophilic amino acid.

Preferably, the amino acid positions to be substituted are selected from the group of positions consisting of Q552, I559, L566, I573, and I580 of HIV-1 and from the group consisting of, L554, Q561, T568, and L575 of HIV-2, respectively.

In a preferred embodiment the present invention relates to a variant of HIV-1 gp41 comprising at least one and at most four amino acid substitution(s) at (a) position(s) selected from the group of positions Leu 555, Leu 566, Ile 573, and Ile 580, wherein these positions are the positions known from the gp41 wild-type sequence described in SEQ ID NO:1 or correspond to these positions known therefrom, characterized in that the substitution amino acid is or respectively and independently are selected from the group consisting of serine, threonine, asparagine, glutamine, aspartic acid and glutamic acid.

This preferred embodiment of the present invention is based on the surprising finding that variants of wild-type gp41 can be provided, which represent significant improvements as compared to the corresponding polypeptide of the gp41 wild-type sequence. The amino acid substitutions leading to the variants of the present invention are described based on the amino acid composition and numbering of the gp41 wild-type sequence as known from Chan, D. C., et al., Cell 89 (1997) 263–73) and given in SEQ ID NO:1.

Obviously, the amino acid substitutions described in the present invention can also be used to substitute amino acids at corresponding sequence positions within gp41 of other known and yet un-identified HIV-1 isolates. The term "corresponding to a position" is used to indicate that HIV-1 isolates and variants thereof may also be found or generated comprising additional amino acids or lacking amino acids, which upon sequence alignment to SEQ ID NO:1 results in a different absolute number for the corresponding sequence position or sequence motif.

The multiple alignment and comparison of a gp41 sequence with the wild-type sequence of SEQ ID NO:1 is performed with the PileUp program of GCG Package Version 10.2 (Genetics Computer Group, Inc.). PileUp creates a multiple sequence alignment using a simplification of the progressive alignment method of Feng, D. F. Doolittle, R. F., J Mol Evol 25 (1987) 351–60, and the scoring matrixes for identical, similar, or different amino acid residues are defined accordingly. This process begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments that include increasingly dissimilar sequences and clusters, until all sequences have been included in the final pairwise alignment. The amino acid positions of a novel HIV-1 isolate or of engineered gp41 molecules which correspond to the positions 555, 566, 573 and 580 of the wild-type sequence thus are easily located.

A preferred variant of an HIV-1 gp41 polypeptide according to the present invention is characterized in that it comprises an amino acid substitution at position 555, wherein Leu 555 is substituted by aspartic acid or by glutamic acid, the substitution by glutamic acid being the most preferred substitution.

A further preferred variant of an HIV-1 gp41 polypeptide according to the present invention is characterized in that it comprises an amino acid substitution at position 566, wherein Leu 566 is substituted by aspartic acid or by glutamic acid, the substitution by glutamic acid being the most preferred substitution.

A further preferred variant of an HIV-1 gp41 polypeptide according to the present invention is characterized in that it comprises an amino acid substitution at position 573, wherein Ile 573 is substituted by serine or by threonine, the substitution by serine being the most preferred substitution.

A further preferred variant of an HIV-1 gp41 polypeptide according to the present invention is characterized in that it comprises an amino acid substitution at position 580, wherein Ile 580 is substituted by aspartic acid or by glutamic acid, the substitution by glutamic acid being the most preferred substitution.

The present invention also relates to a variant of HIV-2 gp36 comprising at least one amino acid substitution and at most three amino acid substitutions at a position selected from the group of positions Leu 554, Leu 565, and Val 579, wherein these positions are the positions known from the HIV-2 gp36 wild-type sequence (SEQ ID NO:2) or correspond to the positions known therefrom, characterized in that the substitution amino acid is or respectively and independently are selected from the group consisting of serine, threonine, asparagine, glutamine, aspartic acid and glutamic acid.

The numbering follows the wild-type sequence (SEQ ID NO:2) published by Guyader, M., et al., Nature 326 (1987) 662–9. Amino acid positions within gp36 which correspond to the positions known from this sequence are determined as described above for gp41.

A preferred variant of an HIV-2 gp36 polypeptide according to the present invention is characterized in that it comprises an amino acid substitution at position 554, wherein Leu 554 is substituted by aspartic acid or by glutamic acid, the substitution by glutamic acid being the most preferred substitution.

A preferred variant of an HIV-2 gp36 polypeptide according to the present invention is characterized in that it comprises an amino acid substitution at position 565, wherein Leu 565 is substituted by aspartic acid or by glutamic acid, the substitution by glutamic acid being the most preferred substitution.

A preferred variant of an HIV-2 gp36 polypeptide according to the present invention is characterized in that it comprises an amino acid substitution at position 579, wherein Val 579 is substituted by aspartic acid or by glutamic acid, the substitution by glutamic acid being the most preferred substitution. In a preferred embodiment the variant gp41 or the variant gp36, respectively, comprises substitutions at two of the amino acid positions, as described above. Variants comprising three amino acid substitutions are also preferred. In yet a further preferred embodiment the variant gp41 comprises substitutions at the four amino acid positions discussed in detail above.

In a preferred embodiment, the complete sequence of gp41 or gp36, respectively, (i.e., the ectodomain lacking the fusion peptide and the transmembrane segment) or of a corresponding mammalian immunodeficiency viral envelope protein (e.g., gp21 from HTLV), is used to form a complex with a PPI chaperone. It is also conceivable to use fragments of a retroviral surface glycoprotein such as the one for gp41 from HIV-1 described by Lu et al., supra. Such fragments preferably comprise the C-terminal helix as well as the N-terminal helix of the extracellular part of gp41.

A diagnostically relevant gp41 comprising the amino acid positions 535 to 681 (nomenclature according to Chan, D. C., et al., Cell 89 (1997) 263–73) may be produced by recombinant techniques according to standard procedures. As described in FIG. 1 of Lu et al., supra, another interesting gp41 molecule spans the amino acids 540–669 of the gp160 precursor molecule.

As a typical example for a retroviral surface glycoprotein, the small envelope protein of HIV is extremely difficult to handle and exhibits quite unusual properties. As already mentioned, one of the most critical features of the e-gp41 molecule is its insolubility at physiological buffer conditions. Recombinantly produced gp41 is both soluble and displays a native-like structure at pH 3.0 and low ionic strength. However, even at this pH, it remains sensitive to the salt concentration in the buffer. Dependent on the salt used, gp41 precipitates in the presence of more than 100 to 500 mM salt. As will be discussed in more detail below, it can (again) be solubilized (in denatured form) by chaotropic agents.

Physiological buffer conditions usually are understood to correspond to salt and pH-conditions found in plasma or serum of animals and are defined by a pH value of around 7.4 and a salt concentration of about 150 mM. The rsgp-chaperone complex according to the present invention is readily soluble under these buffer conditions. The rsgp present therein is immunologically active, thus pointing to a native-like structure. Whereas gp41 in the absence of, or without pre-treatment by, an appropriate detergent is essentially insoluble under physiological buffer conditions (e.g., 20 mM sodium phosphate pH 7.4, 150 mM NaCl), the described complex according to this invention is readily soluble after refolding according to the appropriate protocol. The gp41 ectodomain, as comprised in the inventive complex, is soluble at least at a concentration of 100 nM, preferably at a concentration of 1 $\mu$M and above, most preferred at 10 $\mu$M or more. Thus, solubility is substantially increased from sub-nanomolar to about micromolar concentrations.

For a better understanding of the scope of the present invention, it is necessary to emphasize that the buffer conditions applied for solubilization and renaturation may be modified as required and appropriate and must not be understood as an undue restriction of the invention, which is carried out successfully over a broad range of buffer conditions.

The overall salt concentration of the physiological buffer is not critical as long as care is taken that the chaperone-gp41 complex is not dissociated, and gp41 stays in solution. Preferably the physiological buffer comprises at least 10 mM of the buffer system and at most 200 mM. The rest of the buffer constituents, if any, may be a salt without significant buffer capacity, e.g., sodium chloride. The physiological buffer preferably has a salt concentration between 20 and 500 mM, more preferred between 50 and 300 mM, and most preferred between 100 and 200 mM.

In a process according to the present invention, the physiological buffer may be varied to have a pH value in the range of 5.0 to 8.5; more preferred, the range of such buffer is between pH 5.5 and pH 8.3. Even more preferred, such physiological buffer conditions are defined by the salt concentrations as given above and a pH value between 6.0 and 8.0; most preferred, the pH of such physiological buffer is between 6.5 and 7.8.

According to a process as described in the present invention, a retroviral surface glycoprotein is solubilized under non-physiological buffer conditions, the chaperone is added (or already present as a covalently linked further protein domain), and the mixture comprising the solubilized retroviral surface glycoprotein and the chaperone is then adjusted to physiological buffer conditions. Whereas a retroviral surface glycoprotein alone would spontaneously precipitate when doing so, it surprisingly stays in solution in the above process. This important finding is most likely due to the formation of a complex between retroviral surface glycoprotein and the chaperone.

In case of the recombinant production of gp41 in E. coli, the recombinantly produced gp41 is obtained in the form of inclusion bodies. This material is solubilized using a highly chaotropic reagent, e.g., 7.0 M guanidinium thiocyanate. The gp41 polypeptide is largely unstructured under these conditions. By changing the buffer in appropriate steps to 30 mM formic acid at pH 3.0, the gp41 in solution assumes what is perceived as its native like all-helical structure. One easy way to monitor the status of correct or incorrect folding of a protein is to analyze the corresponding CD spectrum in the amidic (185–250 nm) and the aromatic (260–320 nm) regions. Besides, information on light-straying particles (like aggregates) can easily be obtained from standard UV spectra.

What is important to emphasize here is the fact that the retroviral surface glycoprotein within the retroviral surface glycoprotein-chaperone complex, according to the present invention, does adopt what is considered to be a native-like fold. On the contrary, retroviral surface glycoprotein, which has been solubilized at neutral pH by chaotropic agents, is largely unstructured, thus losing ordered conformation epitopes. It is also possible to solubilize a retroviral surface glycoprotein alternatively by using detergents. For example, sodium dodecyl sulfate (SDS) has successfully been used to solubilize gp41. However, such "SDS-solubilized material" is not the material of choice, e.g., for use in an immunoassay for detection of antibodies to gp41. Furthermore (as discussed above) such immunoassays preferably also detect antibodies to conformational epitopes of gp41, and it cannot be excluded that detergents do partially abolish conformational epitopes.

Preferably, the rsgp-chaperone complex according to the present invention is characterized by the rsgp being native-like folded. The native-like folded rsgp within such a complex, e.g., exhibits the required immunological or physical features.

Native-like folding is preferably assessed by near UV CD spectroscopy, which reports on tertiary contacts within compact globular proteins. It is known that gp41 is readily soluble at about pH 3.0 and a salt concentration of low ionic strength. Near UV CD data demonstrate that under such buffer conditions, gp41 exhibits a characteristic ellipticity signal with the typical signature of a native-like folded globular protein. As shown in FIG. 5, the gp41 part of a fusion peptide comprising gp41 and FkpA exhibits this typical near UV CD spectrum in acidic buffer. Under physiological buffer conditions, the near UV CD spectrum of a soluble complex according to the present invention is composed of both the spectra of the correctly folded chaperone and the native-like folded gp41. This is shown for the FkpA-gp41 fusion protein in FIG. 7.

In a preferred embodiment according to the present invention the native-like fold of gp41 in a gp41-chaperone complex is assessed by analyzing the near UV CD. It is preferred that this near UV CD is used to demonstrate that both molecules gp41 and chaperone are native-like folded.

Production of the soluble chaperone-gp41 complex starts from non-physiological buffer conditions. In the case of complex formation between free chaperone and free target protein (e.g. gp41 from HIV-1), the "non-physiological" buffer has to meet two requirements, that (a) gp41 is present in its native-like acidic structure, and (b) the PPI chaperone is at least partially functional (i.e. binding-competent). Starting from such buffer conditions, the chaperone binds to the amyloidogenic protein, and a change of the buffer conditions from non-physiological to more or less physiological conditions is possible without precipitation of the amyloidogenic protein.

Whereas chaperones usually bind to denatured proteins and act upon them, thereby facilitating their correct (re-) folding, the situation on which the present invention is based is strikingly different. The gp41 solubilized under appropriate non-physiological buffer conditions seems to be present in a native-like form (cf. FIGS. 1A and 1B and FIG. 5). Different from the customary view of chaperone functions, in the inventive method the chaperone appears to bind to the native-like folded protein and to stabilize this protein at buffer conditions under which gp41 is otherwise insoluble and precipitates.

In a preferred embodiment according to the present invention, the PPI chaperone is selected from the group comprising FkpA, SlyD and trigger factor.

It has been found that especially FkpA or SlyD improve the solubility of gp41 and form rather stable complexes therewith. A further preferred embodiment therefore is characterized in that the chaperone is selected from the group comprising FkpA and SlyD. Most preferred is the chaperone FkpA.

As described further above, also fragments of chaperones may be used to bring about the desired function. In case of the modular chaperones, like the FKBPs, comprising a catalytic module and a binding module, it is preferred that such fragments at least comprise the binding domain, or that these fragments at least exhibit essentially a function comparable to the binding domain.

FKBP12 is a human member of the FKBP family and essentially comprises the catalytic isomerase domain of a PPIase. Since it lacks an additional polypeptide-binding domain, it displays significantly reduced binding affinity towards unfolded or partially folded protein substrates as compared to other members of the FKBP family. It has been shown that unfolding and refolding of FKBP12 is a reversible process (Egan, D. A., et al., Biochemistry 32 (1993) 1920–7; Scholz, C., et al., J Biol Chem 271 (1996) 12703–7). We find that refolding and unfolding of FkpA (25–270) and SlyD (1–165) are reversible either, thus fulfilling a pivotal requisite of the process described here.

In a preferred embodiment, the present invention relates to a soluble complex comprising gp41 and a chaperone selected from the FKBP family.

As described above, such soluble complexes comprising gp41 from HIV-1, or a homologue derived from another mammalian immunodeficiency virus, can be easily prepared by mixing the PPI chaperone (e.g., produced by recombinant techniques) and a recombinantly produced gp41. The complex then is formed between two independent molecules, i.e., intermolecularly.

Complex formation is a dynamic process in which dissociation and re-association occur in parallel. This is true for both the intermolecular and the intramolecular (e.g., in a fusion construct) association between, e.g., FkpA and gp41. Since gp41 immediately and quantitatively precipitates from a physiological buffer solution, concentrations of both partners have to be chosen which ensure that only a non-critical or non-aggregating concentration of gp41 in free form is present, and that the vast majority of gp41 is bound and stabilized in form of a gp41-chaperone complex.

Depending on the chaperone used, it has been found necessary to mix on a molar basis at least 2 times as many chaperones as compared to gp41 molecules. In a preferred embodiment, the invention therefore relates to a reagent comprising a mixture of gp41 and a chaperone, preferably FkpA. Preferably such mixture contains FkpA in molar excess as compared to gp41. It is preferred that 3 to 10 times more FkpA is present. The most preferred molar ratio of FkpA to gp41 is between 4 and 6.

It has been also found that the formation of an intramolecular complex, e.g., between the different domains of a protein comprising covalently linked at least one rsgp domain and at least one PPI-chaperone domain, leads to additional advantageous effects, for example in terms of stability and ease of production. It has, for example, been found that a ratio of 1:1 (rsgp to chaperone) is sufficient to form the soluble complex if both domains are covalently linked.

A soluble complex comprising a retroviral surface glycoprotein and a chaperone in a recombinantly linked form represents a further preferred embodiment according to the present invention. Most preferred rsgps comprised in such a recombinant polypeptide are gp41 from HIV-1 and gp36 from HIV-2.

For a recombinant protein comprising at least one rsgp domain and at least one PPI-chaperone domain the transfer from non-physiological to physiological buffer conditions can be accomplished in different ways. Soluble intramolecular complexes between gp41 and FkpA are easily obtained by adjusting the non-physiological buffer conditions to physiological buffer conditions by dialysis, rapid dilution or matrix-assisted refolding. The mixture comprising the soluble gp41-chaperone complex can be directly used for modification.

A soluble complex comprising, e.g., gp41 and a PPI chaperone according to the present invention, can also be produced starting from one polypeptide comprising both protein domains (gp41 and chaperone) obtained by recombinant techniques. The gp41-chaperone complex therein is intramolecular in nature. Preferably the recombinant polypeptide according to the present invention comprises gp41 and a chaperone or gp36 and a chaperone. In yet a further preferred embodiment the present invention relates to a recombinant protein comprising at least one rsgp domain and at least two PPI-chaperone domains. Recombinant polypetides comprising one rsgp domain and two PPI-chaperones are also preferred.

The recombinant polypeptide used to obtain a soluble gp41-chaperone complex according to the present invention is expressed, applying standard molecular biology techniques. Preferably the chaperone gene is placed in frame upstream the target protein gene into an expression vector comprising both the genetic information for gp41 and the chaperone and optionally also the genetic information for an appropriate peptidic linker sequence. A preferred host for large-scale production of such a recombinant fusion protein is *E. coli*.

In a preferred embodiment, the present invention relates to a soluble complex comprising gp41 or gp36, respectively, and a chaperone selected from the peptidyl prolyl isomerase class of chaperones. It is yet further preferred that this soluble complex is an intramolecular complex, preferably an intramolecular complex within a recombinant polypeptide comprising gp41 or gp36 and a PPI chaperone. Most preferred, the PPI chaperone part of the recombinant polypeptide lacks any export signal peptide (of the corresponding precursor molecule) and corresponds to the mature PPI chaperone. Since in this preferred embodiment the recombinant protein lacks a functional signal sequence, the gene product accumulates in the bacterial cytosol.

A striking feature of gp41 comprised in a recombinantly produced FkpA-gp41 is its exceptional solubility as compared to the "unchaperoned" gp41 ectodomain. It is interesting that the "chaotropic material" (i.e. FkpA-gp41 in 6.0–7.0 M GuHCl) can be refolded in different ways, all resulting in a thermodynamically stable and soluble native-like form. Refolding is achieved at high yields, both by dialysis and by rapid dilution, as well as by renaturing size exclusion chromatography or matrix-assisted refolding. These findings suggest that in this covalently linked form, the gp41-FkpA fusion polypeptide is a thermodynamically stable rather than a metastable protein.

The recombinant FkpA-gp41 polypeptide comprises two protein domains having different folding requirements. Since the purification protocol includes an initial denaturation step, it is mandatory that the folding of the chaperone be reversible. Indeed, there is compelling spectroscopic evidence for the reversible and independent refolding of both FkpA and gp41 within the covalently linked protein complex. Refolding of a C-terminally truncated SlyD has been found to be reversible, either.

Also preferred is a recombinant polypeptide comprising a retroviral surface glycoprotein and a chaperone that additionally comprises an appropriate peptide linker sequence between these two polypeptide domains. Such a peptide linker sequence is selected to ensure optimal intramolecular association of the rsgp and the chaperone domain used. Preferably, such a linker sequence is about 20 amino acids long and comprises amino acids supporting both flexibility and solubility, such as e.g., glycine and serine. Preferably the linker is 10 to 50 amino acids in length. More preferred, the length is 12 to 40 amino acids, and most preferred, the linker comprises 15 to 35 amino acids. Both the rsgp and the chaperone are always in close proximity (held together, e.g., by an appropriate linker). In a preferred embodiment the recombinant polypeptide comprises mature FkpA linked to its target protein via a flexible linker. This, as the data indicate, brings about an additional stabilizing effect.

It has surprisingly been found that gp41, as part of the intramolecular complex between a PPI chaperone and gp41, is both soluble and stable. The same holds true for an intramolecular complex comprising a PPI chaperone and gp36 or a PPI chaperone and gp21 from HTLV. The improved stability of gp41 in such a complex brings about additional advantages. For example, it is possible to obtain a fully renatured recombinant gp41-chaperone molecule very easily. The recombinant protein is initially solubilized by treatment with a chaotropic agent (e.g., guanidinium chloride). By simply passing the solubilized material over a gel filtration column, equilibrated with the appropriate physiological buffer, a fully re-natured protein comprising the covalently linked protein domains can be obtained (cf. Example 2.3 and FIGS. 7 and 8).

The soluble intramolecular gp41-chaperone complex exhibits yet a further striking advantage: it is rather stable against the denaturing effects of detergents. This effects becomes even more pronounced, if the fusion protein contains two chaperones and one gp41 or one gp36, respectively. Most immunoassays are performed in the presence of detergents in order to reduce, and at least partially avoid, problems caused by non-specific binding. In the case of HIV diagnosis, rather strong detergents are used because of the aforementioned reason, but also to desintegrate and disrupt virus particles and thus to facilitate detection of viral antigens, like gp24.

The recombinantly produced gp41 ectodomain solubilized by SDS (sodium dodecyl sulfate) is not immunoreactive in an assay buffer routinely used, e.g., in the detection of anti-HIV-antibodies or p24 antigen. cf. FIG. 9). Under the same buffer conditions, however, the gp41, which is part of an intramolecular complex with a PPI chaperone according to this invention, is strongly immunoreactive. As can be seen from FIG. 9, under the same assay conditions and with the same patient serum, this material yields excellent competition curves, which can only be explained by the presence of a native-like soluble gp41, which in addition is stable in the presence of the detergent tested.

It is a very important feature of the complex, according to the present invention, that rsgp within the soluble rsgp-chaperone complex is native-like folded under physiological buffer conditions, e.g., at pH 7.4 in 20 mM phosphate 150 mM sodium chloride buffer. This is a tremendous advantage for therapeutic as well as for diagnostic applications. In a preferred embodiment, the present invention relates to a composition of reagents that is soluble under physiological buffer conditions, comprising an intra- or an inter-molecular complex comprising a retroviral surface glycoprotein and a chaperone selected from the peptidyl prolyl isomerase class of chaperones.

A soluble complex comprising native-like folded gp41 from HIV-1 and a chaperone selected from the peptidyl prolyl isomerase class of chaperones therefore represents a very preferred embodiment of the present invention.

A soluble complex comprising native-like folded gp36 from HIV-2 and a chaperone selected from the peptidyl prolyl isomerase class of chaperones therefore also represents a very preferred embodiment of the present invention.

In terms of therapy, the progress made by providing a "soluble and native-like folded" gp41 or gp36, respectively, is quite obvious. For the first time, e.g., gp41 is now available for injection under physiological buffer conditions.

In a preferred embodiment, the soluble complex as described is used to produce a composition of reagents for use as a medicament. The composition of reagents comprises the gp41-chaperone complex together with physiologically acceptable excipients and, where appropriate, suitable additives and/or conventional auxiliary substances.

It is known that peptides derived from the gp41 heptad repeat or from the gp41 C-terminal helix possess antiviral activity (Wild, C., et al., Proc Natl Acad Sci USA 89 (1992) 10537–41). They hinder virus entry by specifically interacting with a so-called "hairpin-intermediate" of gp41 (for review see Doms, R. W. and Moore, J. P., J Cell Biol 151 (2000) F9–14). We have found that a rsgp-chaperone complex according to the present invention exhibits antiviral activity. The composition of reagents containing the gp41-chaperone complex or a gp36-chaperone complex or both in a therapeutically effective dose in a first preferred therapeutic application is used to prevent HIV entry and HIV spread within the host organism ("virus entry inhibition").

It represents a further preferred therapeutic application of a composition of reagents comprising a gp41-chaperone complex to use such a composition for eliciting an immune response in a mammal. The complex described makes available much more gp41 epitopes than any other HIV immunogen known, cf., e.g., Root et al., supra. The novel immunogen therefore is expected to induce a much broader immune response.

With respect to diagnostic procedures, obvious advantages of a soluble rsgp-chaperone complex according to the present invention are, e.g., the increased stability of a retroviral surface glycoprotein, such as gp41 under physiological buffer conditions, and/or the increase in diagnostic sensitivity, and/or the increased numbers of conformational epitopes present, and/or the possibility to easily label a correctly folded rsgp, like gp41.

Well-known labels are marker groups or effector groups, like solid phase binding groups. A labeled soluble rsgp-chaperone complex represents a further preferred embodiment according to the present invention.

The labeling group can be selected from any known detectable marker groups, such as dyes, luminescent labeling groups such as chemiluminescent groups, e.g., acridinium esters or dioxetanes, or fluorescent dyes, e.g., fluorescein, coumarin, rhodamine, oxazine, resorufin, cyanine and derivatives thereof. Other examples of labeling groups are luminescent metal complexes, such as ruthenium or europium complexes, enzymes, e.g., as used for ELISA or for CEDIA (Cloned Enzyme Donor Immunoassay, e.g., EP-A-0 061 888), and radioisotopes.

Effector groups comprise, for example, one partner of a bioaffine binding pair. While performing an assay, the effector group interacts specifically and preferably non-covalently with the other partner of the bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. Preferred binding pair members comprise hapten, antigen and hormone. Especially preferred are haptens like digoxin and biotin and analogues thereof.

The soluble complex comprising rsgp and a PPI chaperone is preferably used in an immunoassay for detection of antibodies to the rsgp. Preferably gp41- and/or gp36-chaperone complexes are used. In a very preferred embodiment, a labeled soluble complex comprising gp41 and a PPI chaperone is used in an immunoassay for detection of antibodies to gp41. Most preferred, the labeled complex is an intramolecular complex within a recombinant polypeptide comprising the PPI chaperone and gp41.

Immunoassays are well known to the skilled artisan. Methods for carrying out such assays as well as practical applications and procedures are summarized in related textbooks. Examples of related textbooks are Tijssen, P., Preparation of enzym-antibody or other enzyme-macromolecule conjugates in "Practice and theory of enzyme immunoassays" (1990) 221–278, Eds. R. H. Burdon and v. P. H. Knippenberg, Elsevier, Amsterdam) and various volumes of Tijssen, in "Methods in Enzymology" (1980), Eds. S. P. Colowick, N. O. Caplan and S. P., Academic Press), dealing with immunological detection methods, especially volumes 70, 73, 74, 84, 92 and 121.

The novel soluble rsgp-PPI chaperone complex can be used to improve assays for the detection of anti-HIV antibodies independently of the mode of detection (e.g., radioisotope assay, enzyme immunoassay, electrochemiluminescence assay, etc.) or the assay principle (e.g., test strip assay, sandwich assay, or homogenous assay, etc.).

For the reliable and sensitive early detection of an HIV infection, it is essential to measure both viral antigen as well as anti-viral antibody in bodily fluid samples. The soluble complex according to the present invention enables the detection of anti-gp41 and/or anti-gp36 antibodies, at physiological buffer conditions. The detection of anti-gp41 and/or anti-gp36 antibodies is a valuable part of such combined HIV detection systems. In a preferred embodiment, the present invention therefore relates to HIV detection systems comprising the detection of anti-gp41 and/or anti-gp36 antibodies based on the use of a gp41 and/or a gp36 chaperone complex. Most preferred, the detection of anti-gp41 and/or anti-gp36 antibodies based on such complex is carried out together with the detection of an HIV antigen, preferably the p24 antigen.

As known from the art, antibodies to infectious agents such as bacteria, fungi or viruses, are preferably detected by an assay performed according to the double antigen bridge concept (sometimes this assay concept is also termed double antigen bridge concept, because the two antigens are bridged by an antibody). In such an assay the ability of an antibody to bind at least two different molecules of a given antigen with its two (IgG, IgA, IgE) or 10 (IgM) paratopes is required and used.

Detection of antibodies from bodily fluids according to the bridge concept may be performed in many different assay setups. A simple setup comprises the direct coating of an antigen to a solid phase and the use of the same antigen in a labeled form. Under appropriate assay conditions, an antibody in a sample forms a bridge between the solid phase bound antigen and the labeled antigen. Therefore, only if the antibody under investigation is present in the sample is a bridge formed, and a signal can be detected.

The basic structures of "solid phase antigen" and the "detection antigen" preferably are the same. For example, a polypeptide comprising one or several epitopes may be used directly or indirectly coated to a solid phase, and the same synthetic polypeptide, however, bound to a label or marker is used as detection antigen. It is also possible to use similar but different antigens, which are immunologically cross-reactive in a double antigen bridge assay. The essential requirement for performing such assays is that the relevant epitope or the relevant epitopes are present on both antigens. Obviously, there are many variants of the double antigen bridge assay format. Such variants comprise, for example, the indirect coating of an antigen to a solid phase. Preferably, a specific binding pair, most preferably the biotin-streptavidin (or -avidin) system, is used to indirectly bind an antigen to a solid phase. On the other hand, the antigen used for detection in such a system may not directly carry a marker (e.g., a radioisotope, enzyme, fluorescent molecule, etc.), but rather may be indirectly detectable by, e.g., carrying a hapten (for example, digoxin). Such indirect detection then, e.g., may be performed by a labeled anti-digoxin antibody.

In a preferred embodiment the present invention relates to an immunoassay according to the double antigen bridge concept, comprising: a first antigen comprising a first chaperone-antigen complex, and a second antigen comprising a second chaperone-antigen complex In a further preferred embodiment, the present invention relates to an immunoassay according to the double antigen bridge concept characterized in that a first chaperone-antigen complex is used as capture antigen and a second chaperone-antigen complex is used as detection antigen.

The chaperone-antigen complexes as described in the present invention not only bring about the solubility of various polypeptides that are otherwise difficult to handle, but they also allow for a very advantageous immunoassay according to the double antigen bridge concept.

It is an especially attractive feature of such an immunoassay according to the double antigen bridge concept, that it is now possible to use different chaperones for complex formation with the solid phase bound antigen and for complex formation with the detection antigen, respectively. Such modification of an assay further improves upon the problem of non-specific binding. Antibodies in a sample, which would be reactive to a chaperone and thus might cause a false positive signal, will not form a bridge if different chaperones are used to complex the solid phase antigen and the detection antigen, respectively. Therefore, in this mode of the invention, the likelihood of a positive signal due to non-specific binding is largely reduced. In a preferred embodiment, the present invention therefore relates to an immunoassay according to the double antigen bridge concept which is characterized in that the first chaperone and the second chaperone of a first and a second chaperone-antigen complex differ from each other.

Most of the chaperones that are best characterized have been isolated from *Escherichia coli*, which is widely used in biotechnological research. Since *Escherichia coli* is a widely distributed bacterial species, many mammals have developed antibodies against proteins derived from this bacterium. In order to reduce the likelihood of false positive reactions caused by such antibodies, it is preferred to use at least one PPI chaperone derived from a distinct bacterial species, preferably a thermophilic one. Preferably the chaperone is derived from extremophilic bacteria, especially of the group of bacteria comprising *Thermatoga maritima, Aquifex aeolicus* and *Thermus thermophilus*.

The use of a chaperone-antigen complex in an immunoassay in general, and preferably in an immunoassay according to the bridge concept, also provides the possibility to derivatise the chaperone of such a complex and does not require the modification of the antigen itself. It is generally accepted that the modification of a polypeptide by a second chemical moiety, for example, the coupling of a label to that molecule, includes the risk of negatively influencing the polypeptide. For example, the epitope under investigation may be compromised, or non-specific binding may be caused by such labeling. According to the present invention, it is now possible to derivatise specifically the chaperone within a chaperone-antigen complex.

In a preferred embodiment, an immunoassay according to the double antigen bridge concept is further characterized in that the first chaperone-antigen complex used as capture antigen comprises a solid phase binding group.

In a further preferred embodiment, an immunoassay according to the bridge concept is performed, which is further characterized in that the second chaperone-antigen complex used as detection antigen comprises a marker group.

In another embodiment, a soluble complex comprising rsgp and a PPI chaperon, such as gp41- and/or gp36-chaperone complexes, may also be used to elicit an immune response in a subject, such as a human or non-human animal. The soluble complexes may be administered to a subject in compositions, such as those that may contain an excipient or carrier. Such compositions may also include an adjuvant. Examples of conventional adjuvants include, but are not limited to, Freund's incomplete, Freund's complete, Merck 65, AS-2, alum, aluminum phosphate, mineral gels such as aluminum hydroxide, and surface active substances such as lysolecithin, pluronic polyols, polyanions, peptides, oil emulsions, keyhole limpet hemocyanin, and dinitrophenol. Other useful adjuvants include, but are not limited to, bacterial capsular polysaccharides, dextran, IL-12, GM-CSF, CD40 ligand, IFN-γ, IL-1, IL-2, IL-3, IL-4, IL-10, IL-13, IL-18 or any cytokine or bacterial DNA fragment.

One dose (administration) of a soluble complex composition may be given. However, the first administration may be followed by boosting doses, such as once, twice, three times or more. The number of doses administered to a subject depends on in part by the response of a subject to a soluble complex composition. Within the scope of the present invention, a suitable number of doses includes any number required to immunize an animal to soluble complex.

A second administration (booster) of the soluble complex composition may be given between about 7 days and 1 year after the first administration. The time between the first and second administrations may be 14 days to 6 months, 21 days and 3 months, often between about 28 days and 2 months after the original administration. A third administration (second booster) may be given between about 14 days and 10 years after the first administration, e.g., between about 14 days and 3 years, often between about 21 days and 1 year, very often between about 28 days and 6 months after the first administration. Subsequent boosters may be administered at 2 week intervals, or 1 month, 3 month or 6 month to 10 year intervals.

Typically, the amount of soluble complex will be administered to a subject that is sufficient to immunize an animal against an antigen (i.e., an "immunologically effective dose" or a "therapeutically effective dose"). An amount adequate to accomplish an "immunologically effective dose" will depend in part on the weight and general state of health of the subject, and the judgment of the prescribing physician or other qualified personnel.

The effective dose of the soluble complex can be formulated in animal models to achieve an induction of an immune response; such data can be used to readily optimize administration to humans based on animal data. A dose will typically be between about 1 fg and about 100 μg, often between about 1 pg and about 100 μg, more often between about 1 ng and about 50 μg, and usually between about 100 ng and about 50 μg. In some embodiments, the dose is between about 1 fg and about 100 μg per kg subject body weight, often between about 1 pg and about 100 μg, more often between about 1 ng and about 50 μg, and usually between about 100 ng and about 50 μg per kg subject body weight.

The soluble complex-containing compositions of the invention may be administered in a variety of ways and in various forms. A soluble complex composition may include carriers and excipients, such as buffers, carbohydrates, mannitol, proteins, polypeptides or amino acids such as glycine, antioxidants, bacteriostats, chelating agents, suspending agents, thickening agents and/or preservatives; water, oils, saline solutions, aqueous dextrose and glycerol solutions, other pharmaceutically acceptable auxiliary substances as required to approximate physiological conditions, such as buffering agents, tonicity adjusting agents, wetting agents, etc. A conventional adjuvant may also be incorporated into the composition.

While any suitable carrier may be used to administer the compositions of the invention, the type of carrier will vary depending on the mode of administration. Compounds may also be encapsulated within liposomes. Biodegradable microspheres are convenient in some instances as carriers; for example, such as those described in (Tice et al., U.S. Pat. No. 5,942,252, 1999).

Sterilization of the compositions is desirable, such as that accomplished by conventional techniques, such as sterile filtering. The resulting aqueous solutions may be packaged for use as is, or lyophilized.

The soluble complex compositions of the invention may be administered in a variety of ways, including by injection (e.g., intradermal, subcutaneous, intramuscular, intraperitoneal etc.), by inhalation, by topical administration, by suppository, by using a transdermal patch or by mouth.

When administration is by injection, compositions may be formulated in aqueous solutions, preferably in physiologically compatible buffers such as Hanks solution, Ringer's solution, 20 mM phosphate 150 mM sodium chloride buffer (pH 7.4), or physiological saline buffer. The solution may contain formulatory agents such as suspending, stabilizing and/or dispersing agents. Alternatively, the composition may be in powder form for constitution with a suitable vehicle, e.g., sterile pyrogen-free water, before use. Inhalation-delivered compositions may be as aerosol sprays from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch. For topical administration, the compositions may be formulated as solutions, gels, ointments, creams, suspensions, and the like, as are well known in the art. In some embodiments, administration is by means of a transdermal patch. Suppository compositions may also be formulated to contain conventional suppository bases.

When administration is oral, a composition can be readily formulated by combining the composition with pharmaceutically acceptable carriers. Solid carriers include mannitol, lactose, magnesium stearate, etc.; such carriers enable the formation of tablets, pills, dragees, capsules, liquids, gels, syrups, slurries, suspensions etc., for oral ingestion. Such formulations may be powders, capsules and tablets; suitable excipients include fillers such as sugars, cellulose preparation, granulating agents, and binding agents.

Methods of producing polyclonal and monoclonal antibodies, including binding fragments (e.g., F(ab)2) and single chain versions are well known. However, many antigens are incapable of triggering an adequate antibody response. In one embodiment, a composition comprising a soluble complex of the invention and an antigen is administered to an animal, thus eliciting an immune response in the animal. Polyclonal or monoclonal antibodies are subsequently prepared by standard techniques.

The soluble complex comprising rsgp and a PPI chaperon, such as gp41- and/or gp36-chaperone complexes, may also be used to inhibit viral entry into a cell, such as by inhibiting membrane fusion. The cell may be in vitro, in vivo, or ex vivo. The compositions and methods of administration are similar to those described for compositions and methods used to elicit an immune response. If inhibiting viral entry into a cell is accomplished using vaccination, then adjuvants may be used. For in vitro and ex vivo administrations, one of skill in the art will choose appropriate methods based partly on the cell(s), culture conditions and time constraints (if any). For example, one such useful method would be to formulate liposomes that carry the soluble complexes.

The following examples, references, and figures are provided to aid the understanding of the present invention, the true scope of which is set forth in the appended claims. It is understood that modifications can be made in the procedures set forth without departing from the spirit of the invention.

EXAMPLES

Example 1

Production of a Soluble Intermolecular Complex Comprising gp41 and a PPI Chaperone 1.1 Production of E.coli FkpA FkpA was cloned, expressed and purified according to Bothmann, H. and Pluckthun, A., J Biol Chem 275 (2000) 17100–5 with some minor modifications. For storage, the protein solution was dialyzed against 20 mM $NaH_2PO_4$/NaOH (pH 6.0), 100 mM NaCl and concentrated to 26 mg/ml (1 mM).

For cytosolic expression, the FkpA-coding sequence of the above expression vector was modified to lack the sequence part coding for the signal peptide and to comprise instead only the coding region of mature FkpA.

1.2 Production of gp41 (535–681)-His6 gp41 (535–681)-$His_6$ was cloned and expressed in a T7 promotor-based expression system and accumulated in inclusion bodies in the host cell. The isolated inclusion bodies were dissolved in 6 M guanidinium chloride. The His-tagged protein was purified on a Ni-chelate column, followed by gel filtration in 6 M guanidinium on Sephacryl 100. The protein was refolded by rapid dilution as described by Wingfield, P. T., et al., Protein Sci 6 (1997) 1653–60. The final buffer conditions were 30 mM sodium formiate, pH 3.0. Status of folding was assessed for both buffer conditions using near and far UV CD. As can be seen in FIGS. 1A and 1B, both Far and Near UV CD spectra suggest that gp41 adopts a native-like fold only at pH 3.0 in the absence of chaotropic agent.

1.3 pH-shift of the gp41 Ectodomain (HIV) from pH 3.0 to Physiological pH in the Presence of E. coli FkpA 1.3.1 Control Experiment In a control experiment, soluble e-gp41 (in 30 mM formiate, pH 3.0) was diluted 100-fold into final buffer conditions of 20 mM Sodium phosphate (pH 7.5), 50 mM NaCl, 1 mM EDTA. The final protein concentration was about 1 $\mu$M. UV spectra were recorded after 1 minute and 10 minutes. It is obvious from the UV spectra in FIG. 2 that the unchaperoned ectodomain spontaneously aggregates upon pH shift to neutral. FIG. 2 is meant to emphasize the exceptional aggregation tendency of gp41; the spontaneous aggregation of the molecule proceeds far beyond the stage indicated by the upper line.

1.3.2 Preincubation of gp41 with FkpA at pH 3.0 Enables Shift to Neutral pH

To test for the solubilizing potential of the molecular chaperone FkpA, the ectodomain gp41 and FkpA were mixed in a molar ratio of 1:2 and 1:4 (in 30 mM formiate at a pH of approximately 3.5) and co-incubated for 1 minute. Then, the resulting complex was shifted to neutral pH by 12-fold dilution into buffer conditions of 20 mM sodium phosphate pH (7.4), 50 mM NaCl, 1 mM EDTA. The final concentrations of the binding partners in the test tube were 1 $\mu$M gp41, 2$\mu$M and 4$\mu$M FkpA, respectively. All reactions were carried out at room temperature. After 1 and 10 minutes, UV spectra were recorded to test the gp41 samples for aggregates. From FIGS. 3A and 3B, it is evident that FkpA substantially reduces the aggregation of gp41 in a dose-dependent fashion. Comparable data have been obtained with trigger factor from *Thermatoga maritima* with a C-terminally truncated SlyD from *E. coli*.

Example 2

Recombinant Production of a Covalently Linked gp41-FkpA 2.1 Construction of an Expression Plasmid Comprising FkpA and gp41

In the first step, the restriction site BamHI in the coding region of the mature *E. coli* FkpA from plasmid of Example 1.1 was deleted using the QuikChange site-directed mutagenesis kit of Stratagene (La Jolla, Calif.; USA) with the primers:

| | |
|---|---|
| 5'-gcgggtgttccgggtatcccaccgaattc-3' | (SEQ ID NO:3) |
| 5'-gaattcggtgggatacccggaacacccgc-3' | (SEQ ID NO:4) |

The construct was named EcFkpA($\Delta$BamHI)[GGGS]$_3$.

In a second step, a gene fragment encoding amino acids 535–681 from HIV-1 envelope protein was amplified by PCR from the construct of Example 1.2 using the primers:

| | |
|---|---|
| 5'-cgggatccggtggcggttcaggcggtggctctggtggcggtacgctgacggtacaggccag-3' | (SEQ ID NO:5) |
| 5'-ccgctcgaggtaccacagccaatttgttat-3' | (SEQ ID NO:6) |

The fragment was inserted into EcFkpA(ΔBamHI) [GGGS]₃ using BamHI and XhoI restriction sites.

The codons for glycine-serine linker between FkpA and e-gp41 were inserted with reverse primer for cloning of FkpA and with forward primer for cloning of e-gp41.

The resulting construct was sequenced and found to encode the desired protein.

2.2 Purification of the Fusion Protein

*E. coli* BL21 cells harboring the expression plasmid were grown to a $OD_{600}$ of 0.7, and cytosolic overexpression was induced by adding 1 mM of IPTG at a growth temperature of 37° C. Four hours after induction, the cells were harvested by centrifugation (20 min at 5000 g). The bacterial pellet was resuspended in 50 mM sodium phosphate pH 7.8, 6.0 M GuHCl (guanidinium chloride), 5 mM imidazole and stirred at room temperature (10 min) for complete lysis. After repeated centrifugation (Sorvall SS34, 20000 rpm, 4° C.), the supernatant was filtered (0.8/0.2 μm) and applied to a Ni-NTA-column (NTA: Nitrilotriacetate; Qiagen; Germantown, Md.), pre-equilibrated in lysis buffer. Unspecifically bound proteins were removed in a washing step by applying 10 column volumes of lysis buffer. Finally, the bound target protein was eluted with 50 mM sodium phosphate, pH 2.5, 6.0 M GuHCl, and was collected in 4 ml fractions. The absorbance was recorded at 280 nm.

The resulting acidic and chaotropic solution may be stored at 4° C. for further purification steps or in vitro refolding experiments.

Starting with this unfolded material, different refolding methods, such as dialysis, rapid dilution, renaturing size exclusion chromatography or matrix-assisted refolding can be used and carried out successfully, all of them leading to virtually the same native-like folded and soluble protein.

2.3 Renaturation by Dialysis and Rapid Dilution

Material, solubilized as described above, is transferred into physiological buffer conditions by dialysis. The chosen cut-off value of the dialysis tubing was 4000–6000 Daltons.

To induce refolding of the ectodomain (the gp41 part of the covalently linked gp41 and FkpA protein domains), GuHCl was removed from the eluted protein by dialysis against 50 mM sodium phosphate, pH 2.5, 50 mM NaCl (sodium chloride). It is well known that the isolated ectodomain is all-helical and forms tertiary contacts at this extreme pH. When analyzing recombinantly produced FkpA by means of near UV CD, it was found that FkpA is essentially unstructured under the same conditions. It is surprising that refolding of gp41-FkpA by dialysis results in a readily soluble protein complex comprising the covalently linked gp41 and FkpA protein domains. The UV spectrum (FIG. 4) lacks stray light, i.e., apparent absorption beyond 300 nm. Stray light would be indicative of aggregates, thus the spectrum shown in FIG. 4 implies that the re-folded material does not contain significant amounts of aggregates.

Circular dichroism spectroscopy (CD) is the method of choice to assess both secondary and tertiary structure in proteins. Ellipticity in the aromatic region (260–320 nm) reports on tertiary contacts within a protein (i.e., the globular structure of a regularly folded protein), whereas ellipticity in the amide region reflects regular repetitive elements in the protein backbone, i.e., secondary structure.

The near UV CD spectrum shown in FIG. 5 provides compelling evidence that the ectodomain (in the context of the fusion protein) displays native-like tertiary contacts at pH 2.5. The spectrum of the covalently linked gp41/FkpA protein domains almost coincides with the spectrum of the isolated ectodomain under identical conditions (data not shown). The typical signature of gp41 was found: a maximum of ellipticity at 290 nm, a characteristic shoulder at 285 nm and another maximum at 260 nm reflecting an optically active disulfide bridge. It is important to note that FkpA does not contribute to the near UV signal at all under the respective conditions. In fact, the aromatic ellipticity of FkpA at pH 2.5 virtually equals the baseline (data not shown).

In agreement with the results from the near UV region, the far UV CD of the fusion construct at pH 2.5 points to a largely structured gp41 molecule. The two maxima at 220 nm and 208 nm make up, and correspond to, the typical signature of an all-helical ectodomain (FIG. 6). From the conditions indicated (50 mM sodium phosphate, pH 2.5, 50 mM NaCl), the FkpA-gp41 fusion polypeptide can easily be transfered to physiological buffer conditions by rapid dilution. In conclusion, both near and far UV CD underline that native-like structured gp41 is available (in the context of the fusion protein also containing FkpA) in a very convenient fashion. Interestingly, we find that a native-like fusion polypeptide of the SlyD(1–165)-gp41 type can be obtained even simpler by dialysis of the chaotropic material (dissolved, e.g. in 7.0 M GuHCl) against 50 mM sodium phosphate pH 7.4, 150 mM NaCl at room temperature. The nucleotide sequences of two chaperone-gp41 fusion constructs which performed exceptionally well according to the present invention are depicted in SEQ ID NO:7 and SEQ ID NO:8, respectively.

2.4 Renaturation by Size Exclusion Chromatography (SEC)

Unfolded gp41-FkpA polypeptide (dissolved in 50 mM sodium phosphate, pH 7.8, 7.0 M GuHCl) was applied onto a Superdex 200 gel filtration column equilibrated with 20 mM sodium phosphate, pH 7.4, 50 mM NaCl, 1 mM EDTA. FkpA-gp41 elutes essentially in three main fractions: as a high molecular associate, as an apparent hexamer species and as an apparent trimer species. The apparent trimer fraction was concentrated and assessed for its tertiary structure in a near UV CD measurement (FIG. 7).

The resulting graph is virtually an overlay curve to which both the carrier protein FkpA and the target protein gp41 contribute in a 1:1 ratio. Most fortunately, gp41 displays tertiary structure at neutral pH and is evidently solubilized by the covalently bound chaperone. In other words, the chaperone FkpA seems to accept the native-like structured ectodomain gp41 as a substrate and to solubilize this hard-to-fold protein at a neutral working pH. Thus, a crucial requirement for producing high amounts of soluble gp41 antigen for diagnostic purposes is fulfilled.

The far UV CD of FkpA-gp41 at pH 7.4 (FIG. 8) confirms the near UV CD results in that it shows the additivity of the signal contributions of FkpA and gp41, respectively. As expected, the spectrum is dominated by the highly helical gp41 ectodomain (maximal ellipticity at 220 nm and 208 nm, respectively).

The data obtained with the covalently linked gp41/FkpA protein domains solubilized at pH 7.4 under the conditions mentioned above indicate that FkpA and gp41 behave as independently folding units within the polypeptide construct.

Example 3

Effect of Different Detergents upon Recombinant gp41 and a Recombinant FkpA-gp41 Complex used as Antigen in an Immunoassay 3.1 Competitive-type Immunoassay The COBAS CORE HIV Combi test (Roche Diagnostics GmbH, Germany) provides a convenient means to test for the immunoreactivity of recombinant gp41. In principle, this assay also works according to the double antigen bridge concept for detecting antibodies against gp41 of HIV. The solid phase antigen is directly coated. The detection antigen is a peroxidase-labeled gp41 comprising, however, SDS-solubilized gp41 material.

In immunoassays for detection of HIV, it is highly desirable that the reagents used be readily soluble and stable in an incubation buffer comprising rather high concentrations of detergent. Such detergents, e.g., Triton X-100® or Nonidet P-40®, are used at a concentration of 0.1 to 0.2% for disrupting viral particles.

Both SDS-solubilized gp41 as well as FkpA-gp41 produced as described in Example 1, have been tested as competing antigens in the COBAS CORE HIV Combi assay. In order to do so, instead of the commercial incubation buffer, an incubation buffer comprising 0.1% Triton X 100® in a buffer matrix free of human serum is used. The antigen to be tested is co-incubated with a human serum known to be reactive with gp41.

The gp41-FkpA antigen, in a dose-dependent fashion, strongly quenches the signal in a competitive type assay, whereas the SDS-solubilized gp41 is essentially unreactive (FIG. 9). Fifty percent inhibition is achieved at an FkpA-gp41 antigen concentration of 0.1 $\mu$g/ml, corresponding to a molar concentration of 2.2 nM.

It is remarkable that FkpA-gp41 retains its excellent immunoreactivity after pretreatment with diluent buffer which contains 0.1% Triton X-100 as a detergent (helper detergent) for disintegrating intact viral membranes in the test. This is in marked contrast to the gp41 ectodomain alone (gp41 in SDS), which in the presence of the helper detergent loses its immunoreactivity almost completely (FIG. 9).

It was a major concern in the development of the covalently linked gp41-FkpA construct that either the FkpA would mask crucial epitopes due to insufficient binding dynamics or that the test-inherent detergent Triton X-100 would destroy the test performance by inducing aggregation of the gp41 antigen. The experimental results of many competition tests on the COBAS CORE platform provide compelling evidence that crucial gp41 epitopes are well-accessible in the context of the covalently linked protein domains. Moreover, the immunoreactivity of gp41 within the intramolecular chaperone-gp41 complex is retained in the presence of helper detergents like Triton X-100.

3.2 Electrochemiluminescence Assay

Immunoassays according to the double antigen bridge format are of great advantage in the serological diagnosis of infectious agents. Since FkpA-gp41, according to the present invention is soluble at physiological buffer conditions, it has been possible to investigate whether this material is suitable for use in a double antigen bridge assay employing electrochemiluminescence as a detection principle.

Attempts to couple SDS-solubilized gp41 to Ruthenium-labels have not been successful. Since, however, FkpA-gp41 is readily soluble under physiological buffer conditions, coupling of this material to hydrophobic Ru-labels proved straightforward. It is noteworthy that even the target-chaperone complex modified in the way described remains soluble. In order to perform the assay on the Elecsys® test system (Roche Diagnostics GmbH, Germany), FkpA-gp41 was biotinylated and ruthenylated, respectively, and tested for immunoreactivity in a double antigen bridge assay.

Several representative anti-HIV sera containing mainly IgG (immunoglobulin G) class antibodies tested highly positive with the covalently linked FkpA-gp41 protein domains. It also has been found that the background signal approaches the intrinsic gadget background, even at antigen concentrations as high as 500 ng/ml. The signal-to-noise ratio turned out to be excellent. Moreover, there is no evidence that the carrier protein, the molecular chaperone FkpA from *E. coli*, causes non-specific binding of antibodies contained in these human sera.

As discussed above, the early detection of seroconversion is crucial to the reliable diagnosis of HIV. During the course of infection, antibodies of the IgM class appear first. In order to detect HIV infection reliably in a very early phase, it is therefore mandatory to design an antigen module with high epitope density for IgM recognition and binding. Indeed, FkpA-gp41 is well recognized by typical anti-HIV, IgM-type sera. What is even more important is the fact that samples that are difficult to test positive, like the B and C sera from the 9003 and 4009 seroconversion panel as supplied by NABI (Miami, Fla.), tested positive with the fusion construct according to the present invention. This is a major achievement since gp41 antigens on a peptide basis are not reactive at all when tested with these IgM sera.

Example 4

Soluble Chaperone-gp41 Complexes Inhibit Virus Entry

Different gp41-chaperone fusion proteins were assessed for their ability to inhibit HIV-1-mediated membrane fusion in an in vitro assay. In short, MAGI P4-CCR5 reporter cell lines expressing CD4, CCR5 and CXCR4 were infected with HIV-1 strain NL4-3 and assessed for Tat-dependent β-galactosidase activity according to Meister et al., Virology (2001) 284(2), 287–296. Indeed, we observe a substantial inhibition of infection with $IC_{50}$ values in the nM range. SlyD-gp41, for instance (see SEQ ID NO:6) inhibits virus entry significantly with an $IC_{50}$ of <70 nM.

In conclusion, the soluble intramolecular complex comprising HIV-1 gp41 or HIV-2 gp36, respectively, and a peptidyl-prolyl-isomerase chaperone possesses outstanding properties with respect to solubility and conformational integrity that allow for the design of improved anti-HIV antibody tests and other commercial applications.

Example 5

Fusion of the Chaperone FkpA to the gp36 Ectodomain Yields a Cytosolic Polypeptide that Can Easily be Refolded in vitro In order to obtain gp36, the HIV-2 homologue of gp41, in a soluble and immunologically active form, we cloned a construct termed FF36. This fusion polypeptide comprises two FkpA units and a gp36 unit, each linked by a flexible glycine-rich stretch. To facilitate purification, the fusion construct was tagged with $His_6$ C-terminally. The protein was essentially purified according to the aforementioned protocol: after chaotropic lysis, the protein was bound to a Ni-NTA-column and was—after excessive washing with 50 mM sodium phosphate pH 7.8, 7.0 M GuHCl—eluted by lowering the pH. The eluted protein was then refolded by passing it over a gel filtration column equilibrated with 50 mM sodium phosphate pH 7.8, 100 mM sodium chloride, 1 mM EDTA. The native protein resulting from this "renaturing gel filtration" method displayed satisfying immunological and spectroscopic properties (see FIG. 10), thus corresponding to gp41 counterparts such as F41 or FF41. The purification and refolding protocol as described here was carried out with FF36 bearing three point mutations in the N-terminal heptad repeat region of gp36 (for sequence see SEQ ID NO:9). The same protocol was also successfully applied to a fusion construct comprising the wt gp36 ectodomain, albeit with lower yields of soluble protein.

Example 6

Soluble, Immunoreactive FkpA-gp21 Can be Obtained in a Convenient and Reproducible Fashion FkpA-gp21-overproducing *E. coli* cells (comprising: SEQ ID NO:10) were grown, induced and harvested as described before. For complete lysis, cell pellets were stirred in 50 mM sodium phosphate pH 7.8, 7.0 M GuHCl at room temperature for 1 hour. The chaotropic cell lysate was applied onto a Ni-NTA-column pre-equilibrated in lysis buffer. After the washing step, the target protein (which bears a C-terminal Hexa-His-Tag) was eluted by lowering the pH. For refolding, FkpA-gp21 (stored in 50 mM sodium phosphate pH 6.0, 7.0 M GuHCl at 4° C.) was passed over a Superdex 200 gel filtration column pre-equilibrated in 50 mM sodium phosphate pH 7.8, 100 mM sodium chloride. UV-spectra demonstrated that FkpA-gp21 elutes as a soluble protein which is—in contrast to the unchaperoned gp21—no more prone to aggregation (FIG. 11A). Moreover, the resulting FkpA-gp21 exhibits excellent immunological activity when assessed in a competitive type COBAS CORE experiment (FIG. 11B).

Example 7

Fusion of an Additional FkpA-subunit to FkpA-gp41 Improves Immunological Properties of the gp41 Ectodomain We addressed the question if an additional PPIase subunit within the fusion polypeptide context might improve the overall properties of the gp41 ectodomain-chaperone complex. To this end, we prepared both F41 (one FkpA domain located upstream to the gp41 variant) and FF41 (two FkpA domains located upstream to the gp41 variant) according to the described protocol. The biotinylated and ruthenylated fusion proteins were then assessed in the Elecsys® E2010 system. The results (Table 1) are strongly indicative for improved properties of the FF41 construct, containing an additional chaperone domain.

Background signals with negative sera, which are decisive for signal-to-noise-ratio and reliable measurement of low titer sera, were found to be reduced by more than fifty percent, when FF41 (about 1600 counts) was compared to F41 (about 3800 counts).

TABLE 1

Comparison of F41 and FF41

| | F41 | FF41 |
|---|---|---|
| R1: | EMHR220 | EMHR221 |
| ESS in R1 | F-41-Bi(UE)25 | FF-41-Bi-UEEK |
| β(AL) | 500 ng/ml | 750 ng/ml |
| R2 | EMHR221 | EMHR222 |
| ESS in R2 | F-41-Ru(UE)25 | FF41-2Ru-SK(4) |
| β(AL) | 500 ng/ml | 750 ng/ml |
| Average counts with negative sera | 3,768 | 1,589 |

Similar positive results have been obtained with a SS41 fusion protein, ie. a fusion protein containing two SlyD domains and one gp41 domain C-terminal to the chaperone domains.

REFERENCES

Aslam, M. and Dent, A., The preparation of protein-protein conjugates in "Bioconjugation" (1998) 216–363, Eds. M. Aslam and A. Dent, McMillan Reference, London Bardwell, J. C., Mol Microbiol 14 (1994) 199–205

Beissinger, M. and Buchner, J., Biol. Chem. 379 (1998) 245–59

Bothmann, H. and Pluckthun, A., J Biol Chem 275 (2000) 17100–5

Braden, B. C. and Poljak, R. J., Faseb J 9 (1995) 9–16

Buchner, J., Faseb J 10 (1996) 10–19

Butler, J. E., et al., J. Immunol. Methods 150 (1992) 77–90

Caffrey, M., et al., J Biol Chem 275 (2000) 19877–82

Chan, D. C., et al., Cell 89 (1997) 263–73

Crooke, E. and Wickner, W., Proc Natl Acad Sci USA 84 (1987) 5216–20

Danese, P. N., et al., Genes Dev 9 (1995) 387–98

Dartigalongue, C. and Raina, S., Embo J 17 (1998) 3968–80

Doms, R. W. and Moore, J. P., J Cell Biol 151 (2000) F9–14

Egan, D. A., et al., Biochemistry 32 (1993) 1920–7

Fischer, G., et al., Nature 337 (1989) 476–8

Frech, C., et al., Embo J 15 (1996) 392–98

Gething, M. J. and Sambrook, J., Nature 355 (1992) 33–45

Guyader, M., et al., Nature 326 (1987) 662–9

Hottenrott, S., et al., J Biol Chem 272 (1997) 15697–701

Kay, J. E., Biochem J 314 (1996) 361–85

Lane, W. S., et al., J Protein Chem 10 (1991) 151–60

Lu, M., et al., Nat. Struct. Biol. 2 (1995) 1075–82

Meister, S., et al., Virology 284 (2001) 287–96

Missiakas, D., et al., Embo J 14 (1995) 3415–24

Missiakas, D., et al., Mol Microbiol 21 (1996) 871–84

Prusiner, S. B., Proc Natl Acad Sci USA 95 (1998) 13363–83

Rahfeld, J. U., et al., FEBS Lett 352 (1994) 180–4

Ramm, K. and Pluckthun, A., J Biol Chem 275 (2000) 17106–13

Ratner, L., et al., Nature 313 (1985) 277–84

Root, M. J., et al., Science 291 (2001) 884–8

Schmid, F. X., Molecular chaperones in the life cyle of proteins in "–" (1998) 361–389, Eds. A. L. Fink and Y. Goto, Marcel Decker In., New York Scholz, C., et al., Embo J 16 (1997) 54–8

Scholz, C., et al., J Biol Chem 271 (1996) 12703–7

Stoller, G., et al., Embo J 14 (1995) 4939–48

Tijssen, in "Methods in Enzymology" (1980), Eds. S. P. Colowick, N. O. Caplan and S. P., Academic Press Tijssen, P., Preparation of enzym-antibody or other enzyme-macromolecule conjugates in "Practice and theory of enzyme immunoassays" (1990) 221–278, Eds. R. H. Burdon and v. P. H. Knippenberg, Elsevier, Amsterdam Wang, C. C. and Tsou, C. L., Faseb J 7 (1993) 1515–7

Wild, C., et al., Proc Natl Acad Sci USA 89 (1992) 10537–41

Wingfield, P. T., et al., Protein Sci 6 (1997) 1653–60

Winter, J., et al., Journal of Biotechnology 84 (2000) 175–185

Zarnt, T., et al., J Mol Biol 271 (1997) 827–37

AU 597884

EP 0280211

EP 396 559

U.S. Pat. No. 4,735,896

U.S. Pat. No. 4,879,212

WO 92/22573

WO 93/21346

WO 94/08012

What is claimed is:

1. A method of producing a soluble complex comprising a target protein and a peptidyl prolyl isomerase class chaperone or a binding competent fragment thereof, said method comprising:

mixing the target protein and the chaperone in a non-physiological buffer, wherein both the target protein and the chaperone are solubilized, and adjusting the buffer to physiological conditions, wherein the target protein-chaperone complex formed is soluble to at least 100 nM in a solution which has a pH of 7.4 and consisting of 20 mM sodium phosphate and 150 mM sodium chloride.

2. The method of claim 1, wherein the peptidyl prolyl isomerase chaperone is an FKBP chaperone.

3. The method of claim 2, wherein the FKBP chaperone is selected from the group consisting of SlyD, FkpA and trigger factor.

4. The method of claim 1, wherein the buffer at physiological conditions comprises a buffer compound in a concentration of 10 to 200 mM and a total concentration of salt of 20 to 500 mM.

5. The method of claim 1, the target protein is produced recombinantly.

6. The method of claim 1, wherein the peptidyl prolyl isomerase chaperone is produced recombinantly.

7. The method of claim 1, wherein the target protein and the peptidyl prolyl isomerase chaperone are produced recombinantly.

8. The method of claim 1, wherein the target protein is an amyloidogenic protein.

9. The method of claim 1, wherein the target protein is HIV-2 gp36 or HIV-1 gp41.

10. A method of producing a soluble complex comprising retrovirol surface glycoprotein and a peptidyl prolyl isomerase class chaperone or a binding competent fragment thereof, said method comprising:

mixing a retroviral surface glycoprotein and a peptidyl prolyl isomerase chaperone in a non-physiological buffer, wherein both the retroviral surface glycoprotein and the chaperone are solubilized and form a complex, and adjusting the buffer to physiological conditions, wherein the retroviral surface glycoprotein-chaperone complex formed is soluble to at least 100 nM in a solution which has a pH of 7.4 and consisting of 20 mM sodium phosphate and 150 mM sodium chloride.

11. The method of claim 10, wherein the peptidyl prolyl isomerase chaperone is an FKBP chaperone.

12. The method of claim 11, wherein the FKBP chaperone is selected from the group consisting of SlyD, FkpA and trigger factor.

13. The method of claim 10, wherein the buffer at physiological conditions comprises a buffer compound in a concentration of 10 to 200 mM and a total concentration of salt of 20 to 500 mM.

14. The method of claim 10, wherein the retroviral surface glycoprotein is produced recombinantly.

15. The method of claim 10, wherein the peptidyl prolyl isomerase chaperone is produced recombinantly.

16. The method of claim 10, wherein the retroviral surface glycoprotein and the peptidyl prolyl isomerase chaperone are produced recombinantly.

17. The method of claim 10, wherein the retroviral surface glycoprotein is HIV-2 gp36 or HIV-1 gp41.

18. A method of producing a soluble complex comprising a variant of HIV-1 gp41 protein and a peptidyl prolyl isomerase class chaperone or a binding competent fragment thereof, said method comprising:

mixing the variant of HIV-1 gp41 protein and the chaperone in a non-physiological buffer, wherein both the variant of HIV-1 gp41 protein and the chaperone are solubilized, and adjusting the buffer to physiological conditions, wherein the variant of HIV-1 gp41 protein-chaperone complex formed is soluble to at least 100 nM in a solution which has a pH of 7.4 and consisting of 20 mM sodium phosphate and 150 mM sodium chloride, and wherein the variant comprises 1 to 6 amino acid substitutions selected from the group of positions consisting of Ile548, Gln552, Leu555, Ile559, Gln562, Leu566, Thr569, Ile573, Leu576, and Ile580, said positions corresponding to those positions in wild-type HIV-1 having SEQ ID NO: 1.

19. The method of claim 18, wherein the variant of HIV-1 gp41 protein comprises 1 to 4 amino acid substitutions selected from the group of positions consisting of Leu555, Leu566, Ile573, and Ile580.

20. The method of claim 19, wherein Leu555 is substituted with aspartic acid or glutamic acid.

21. The method of claim 19, wherein Leu566 is substituted with aspartic acid or glutamic acid.

22. The method of claim 19, wherein Ile573 is substituted with serine or threonine.

23. The method of claim 19, wherein Ile580 is substituted with aspartic acid or glutamic acid.

24. The method of claim 19, wherein substitution amino acids(s) is (are) selected from the group consisting of serine, threonine, asparagine, glutamine, aspartic acid, and glutamic acid.

25. The method of claim 18, wherein the peptidyl prolyl isomerase chaperone is an FKBP chaperone.

26. The method of claim 25, wherein the FKBP chaperone is selected from the group consisting of SlyD, FkpA and trigger factor.

27. The method of claim 18, wherein the buffer at physiological conditions comprises a buffer compound in a concentration of 10 to 200 mM and a total concentration of salt of 20 to 500 mM.

28. The method of claim 18, wherein the variant of HIV-1 gp41 protein is produced recombinantly.

29. The method of claim 18, wherein the peptidyl prolyl isomerase chaperone is produced recombinantly.

30. The method of claim 18, wherein the variant of HIV-1 gp41 protein and the peptidyl prolyl isomerase chaperone are produced recombinantly.

31. A method of producing a soluble complex comprising a variant of HIV-2 gp36 protein and a peptidyl prolyl isomerase class chaperone or a binding competent fragment thereof, said method comprising:

mixing the variant of HIV-2 gp36 protein and the chaperone in a non-physiological buffer, wherein both the variant of HIV-2 gp36 protein and the chaperone are solubilized, and adjusting the buffer to physiological conditions, wherein the variant-chaperone complex formed is soluble to at least 100 nM in a solution which has a pH of 7.4 and consisting of 20 mM sodium phosphate and 150 mM sodium chloride, and wherein the variant of HIV-2 gp36 protein comprises 1 to 6 amino acid substitutions selected from the group of positions consisting of Ile547, Gln551, Leu554, Val558, Gln561, Leu565, Thr568, Thr572, Leu575, and Val579, said positions corresponding to those positions in wild-type HIV-2 having SEQ ID NO: 2.

32. The method of claim 31, wherein the variant of HIV-2 gp36 protein comprises 1 to 3 amino acid substitutions selected from the group of positions consisting of Leu554, Leu565, and Val579.

33. The method of claim 32, wherein Leu554 is substituted with aspartic acid or glutamic acid.

34. The method of claim 32, wherein Leu565 is substituted with aspartic acid or glutamic acid.

35. The method of claim 32, wherein Val579 is substituted with aspartic acid or glutamic acid.

36. The method of claim 32, wherein substitution amino acids(s) is (are) selected from the group consisting of serine, threonine, asparagine, glutamine, aspartic acid, and glutamic acid.

37. The method of claim 31, wherein the peptidyl prolyl isomerase chaperone is an FKBP chaperone.

38. The method of claim 37, wherein the FKBP chaperone is selected from the group consisting of SlyD, FkpA and trigger factor.

39. The method of claim 30, wherein the buffer at physiological conditions comprises a buffer compound in a concentration of 10 to 200 mM and a total concentration of salt of 20 to 500 mM.

40. The method of claim 30, wherein the variant of HIV-2 gp36 protein is produced recombinantly.

41. The method of claim 30, wherein the peptidyl prolyl isomerase chaperone is produced recombinantly.

42. The method of claim 30, wherein the variant of HIV-2 gp36 protein and the peptidyl prolyl isomerase chaperone are produced recombinant

UNITED STATES PATENT AND TRADEMARK OFFICE
CERTIFICATE OF CORRECTION

PATENT NO. : 6,962,982 B2 Page 1 of 1
APPLICATION NO. : 10/179905
DATED : November 8, 2005
INVENTOR(S) : Christian Scholz et al.

It is certified that error appears in the above-identified patent and that said Letters Patent is hereby corrected as shown below:

<u>On the Title Page item (56), under other Publications</u>

On page 2, column 2, line 14, delete "Rool" and substitute --Root-- in its place.

Signed and Sealed this

Fourth Day of March, 2008

JON W. DUDAS
*Director of the United States Patent and Trademark Office*

SEQUENCE LISTING

<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:primer1

<400> SEQUENCE: 1
gcgggtgttc cgggtatccc accgaattc                                29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:primer2

<400> SEQUENCE: 2
gaattcggtg ggatacccgg aacacccgc                                29

<210> SEQ ID NO 3
<211> LENGTH: 61
<212> TYPE: DNA
<213> ORGANISM: Artificial Sequence
<220> FEATURE:
<223> OTHER INFORMATION: Description of Artificial Sequence:primer3

<400> SEQUENCE: 3
cgggatccgg tggcggttca ggcggtggct ctggtggcgg tacgctgacg gtacaggcca    60
g                                                                   61

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:primer4

<400> SEQUENCE: 4
ccgctcgagg taccacagcc aatttgttat                               30

<210> SEQ ID NO 5
<211> LENGTH: 1269
<212> TYPE: DNA
<213> ORGANISM: Artificial Sequence
<220> FEATURE:
<223> OTHER INFORMATION: Description of Artificial Sequence:fusion
      protein FkpA-gp41

<400> SEQUENCE: 5
atggctgaag ctgcaaaaacc tgctacaact gctgacagca agcagcgtt caaaaatgac    60 gatcagaaat cagcttatgc actgggtgct tcgctgggtc gttacatgga aaactctctt   120
aaagaacaag aaaaactggg catcaaactg gataaagatc agctgatcgc tggtgttcag   180
gatgcatttg ctgataagag caaactctcc gaccaagaga tcgaacagac tctgcaagca   240
ttcgaagctc gcgtgaagtc ttctgctcag gcgaagatgg aaaaagacgc ggctgataac   300
gaagcaaaag gtaaagagta ccgcgagaaa tttgccaaag agaaaggtgt gaaaacctct   360
tcaactggtc tggtttatca ggtagtagaa gccggtaaag cgaagcacc gaaagacagc   420

```
gatactgttg tagtgaacta caaaggtacg ctgatcgacg gtaaagagtt cgacaactct    480
tacacccgtg gtgaaccgct ctctttccgt ctggacggtg ttatcccggg ttggacagaa    540
ggtctgaaga acatcaagaa aggcggtaag atcaaactgg ttattccacc agaactggct    600
tacggcaaag cgggtgttcc gggtatccca ccgaattcta ccctggtgtt tgacgtagag    660
ctgctggatg tgaaaccagc gccgaaggct gatgcaaagc cggaagctga tgcgaaagcc    720
gcagattctg ctaaaaaagg tggcggttcc ggcggtggct ctggtggcgg atccggtggc    780
ggttccggcg gtggctctgg tggcggtacg ctgacggtac aggccagaca attattgtct    840
ggtatagtgc agcagcagaa caatgagctg agggctattg aggcgcaaca gcatctggag    900
caactcacag tctggggcac caagcagctc caggcaagag aactggctgt ggaaagatac    960
ctaaaggatc aacagctcct ggggatttgg ggttgctctg gaaaactcat ttgcaccact   1020
gctgtgcctt ggaatgctag ttggagtaat aaatctctgg aacagatttg gaataacatg   1080
acctggatgg agtgggacag agaaattaac aattacacaa gcttaataca ttccttaatt   1140
gaagaatcgc aaaaccagca agaaaagaat gaacaagaat tattggaatt agataaatgg   1200
gcaagtttgt ggaattggtt taacataaca aattggctgt ggtacctcga gcaccaccac   1260
caccaccac                                                           1269

<210> SEQ ID NO 6
<211> LENGTH: 1026
<212> TYPE: DNA
<213> ORGANISM: Artificial Sequence
<220> FEATURE:
<223> OTHER INFORMATION: Description of Artificial Sequence:fusion
      protein SlyD-gp41

<400> SEQUENCE: 6
atgaaagtag caaaagacct ggtggtcagc ctggcctatc aggtacgtac agaagacggt     60
gtgttggttg atgagtctcc ggtgagtgcg ccgctggact acctgcatgg tcacggttcc    120
ctgatctctg gcctggaaac ggcgctggaa ggtcatgaag ttggcgacaa atttgatgtc    180
gctgttggcg cgaacgacgc ttacggtcag tacgacgaaa acctggtgca acgtgttcct    240
aaagacgtat ttatgggcgt tgatgaactg caggtaggta tgcgtttcct ggctgaaacc    300
gaccagggtc cggtaccggt tgaaatcact gcggttgaag acgatcacgt cgtggttgat    360
ggtaaccaca tgctggccgg tcagaacctg aaattcaacg ttgaagttgt ggcgattcgc    420
gaagcgactg aagaagaact ggctcatggt cacgttcacg gcgcgcacga tcaccaccac    480
gatcacgacc acgacggtgg cggttccggc ggtggctctg gtgcggatc cggtggcggt    540 tccggcggtg gctctggtgg cggtacgctg acggtacagg ccagacaatt attgtctggt    600
atagtgcagc agcagaacaa tgagctgagg gctattgagg cgcaacagca tctggagcaa    660
ctcacagtct ggggcaccaa gcagctccag gcaagagaac tggctgtgga aagataccta    720
aaggatcaac agctcctggg gatttgggt tgctctggaa aactcatttg caccactgct    780
gtgccttgga atgctagttg gagtaataaa tctctggaac agatttggaa taacatgacc    840
tggatggagt gggacagaga aattaacaat tacacaagct taatacattc cttaattgaa    900
gaatcgcaaa accagcaaga aaagaatgaa caagaattat tggaattaga taaatgggca    960
agtttgtgga attggtttaa cataacaaat tggctgtggt acctcgagca ccaccaccac   1020
caccac                                                              1026
```